(12) United States Patent
Kawai

(10) Patent No.: US 8,622,895 B2
(45) Date of Patent: Jan. 7, 2014

(54) ELECTRIC BENDING ENDOSCOPE

(75) Inventor: Toshimasa Kawai, Yokohama (JP)

(73) Assignee: Olympus Medical Systems Corp., Tokyo (JP)

(*) Notice: Subject to any disclaimer, the term of this patent is extended or adjusted under 35 U.S.C. 154(b) by 842 days.

(21) Appl. No.: 12/167,628

(22) Filed: Jul. 3, 2008

(65) Prior Publication Data
US 2008/0262310 A1  Oct. 23, 2008

Related U.S. Application Data

(63) Continuation of application No. PCT/JP2007/050303, filed on Jan. 12, 2007.

(30) Foreign Application Priority Data

Jan. 13, 2006 (JP) ................................. 2006-006146

(51) Int. Cl.
*A61B 1/00* (2006.01)
(52) U.S. Cl.
USPC ........... 600/152; 600/117; 600/118; 600/139; 600/145; 600/146
(58) Field of Classification Search
USPC .......... 600/101, 117, 118, 139, 145, 146, 152
See application file for complete search history.

(56) References Cited

U.S. PATENT DOCUMENTS

| 4,982,725 | A | * | 1/1991 | Hibino et al. | 600/117 |
| 5,469,840 | A | * | 11/1995 | Tani et al. | 600/117 |
| 5,868,666 | A | * | 2/1999 | Okada et al. | 600/118 |
| 2002/0165432 | A1 | * | 11/2002 | Matsui | 600/145 |
| 2004/0054258 | A1 | | 3/2004 | Maeda et al. | |
| 2006/0074383 | A1 | | 4/2006 | Boulais | |
| 2007/0161861 | A1 | * | 7/2007 | Kawai et al. | 600/145 |
| 2008/0262306 | A1 | * | 10/2008 | Kawai | 600/118 |

FOREIGN PATENT DOCUMENTS

| EP | 1 787 572 A1 | 5/2007 |
| JP | 2000-147058 | 5/2000 |
| JP | 2003-115847 | 4/2003 |
| JP | 2003-245246 | 9/2003 |
| JP | 2005-342147 | 12/2005 |
| WO | WO 2006/019136 A1 | 2/2006 |

OTHER PUBLICATIONS

Supplementary European Search Report mailed Feb. 2, 2012 in corresponding European Patent Application No. 07706645.4.

* cited by examiner

*Primary Examiner* — Philip R Smith
*Assistant Examiner* — Rynae Boler
(74) *Attorney, Agent, or Firm* — Scully, Scott, Murphy & Presser, P.C.

(57) ABSTRACT

In the present invention, a logical block of an FPGA is configured by a serial communication unit, a serial communication control portion, an EEPROM controller, an abnormal signal processing portion, an LED controller, an operation mode controller, a DPRAM, a clutch signal input portion, a jig substrate input output portion, a RAM, a motor controller, a motor drive waveform generating portion, an RL (right and left) motor current F/B portion, a UD (up and down) motor current F/B portion, a potentiometer control portion, a thermistor control portion, an RL encoder control portion, a UD encoder control portion, and an FPGA block abnormality monitoring portion.

8 Claims, 20 Drawing Sheets

ELECTRIC BENDING ENDOSCOPE

CROSS REFERENCE TO RELATED APPLICATION

This application is a continuation application of PCT/JP2007/050303 filed on Jan. 12, 2007 and claims benefit of Japanese Application No. 2006-006146 filed in Japan on Jan. 13, 2006, the entire contents of which are incorporated herein by this reference.

BACKGROUND OF THE INVENTION

1. Field of the Invention

The present invention relates to an electric bending endoscope including an electric bending endoscope in which a bending portion is electrically bent to a state corresponding to an absolute position signal by operating a bending operation instruction portion outputting the absolute position signal.

2. Description of the Related Art

In recent years, there has been widely used an endoscope which is capable of observing an organ in a body cavity by inserting a thin and long insertion portion into the body cavity, and is capable of, when necessary, performing various medical treatments by using a treatment instrument inserted into a treatment instrument channel.

The endoscope is generally provided, on the distal end portion side thereof, with a bending portion which is bent in the up and down/left and right directions. The bending portion can be bent in a desired direction by performing a pulling and slackening operation of a bending wire connected to the bending portion.

Generally, the bending wire has been manually operated. However, in recent years, as disclosed, for example, in Japanese Patent Application Laid-Open Publication No. 2003-245246, there is also an electric bending endoscope in which the pulling operation is performed by using bending power unit, such as an electric motor.

In the electric bending endoscope, the bending portion is bent by such a way that the electric motor is rotated, for example, by using a joystick which is bending operation instruction unit provided in an operation portion and which outputs, for example, a bending instruction signal for an absolute position, and that a pulley is rotated by the rotation of the electric motor to pull the bending wire connected to the pulley.

The joystick instructs a bending position by being tilted. That is, the direction to which the joystick is tilted is a direction to which the bending portion is to be bent, and the tilting angle of the joystick is the bending angle of the bending portion. When the joystick is in the upright state where the tilting angle of the joystick is 0 degrees, the bending portion is in a non-bent state (linear state). Therefore, it is possible for an operator to easily grasp the bending state of the bending portion in the body cavity from the sense of hand fingers which hold the joystick.

SUMMARY OF THE INVENTION

An electric bending endoscope according to the present invention includes: a bending portion provided in an insertion portion; bending drive unit having a plurality of components to bend the bending portion; bending power unit configured to drive the bending drive unit; bending state detecting unit configured to detect operation information of the bending drive unit, and to detect bending state information on the bending portion; instruction unit configured to output bending instruction information for bending the bending portion; and bending operation control unit configured by a plurality of independent logical blocks and configured to perform control to make the bending instruction information of the instruction unit coincident with the bending state information of the bending portion.

BRIEF DESCRIPTION OF THE PREFERRED EMBODIMENT(S)

In the following, embodiments according to the present invention will be described with reference to the accompanying drawings.

Embodiment 1

Figure 1:
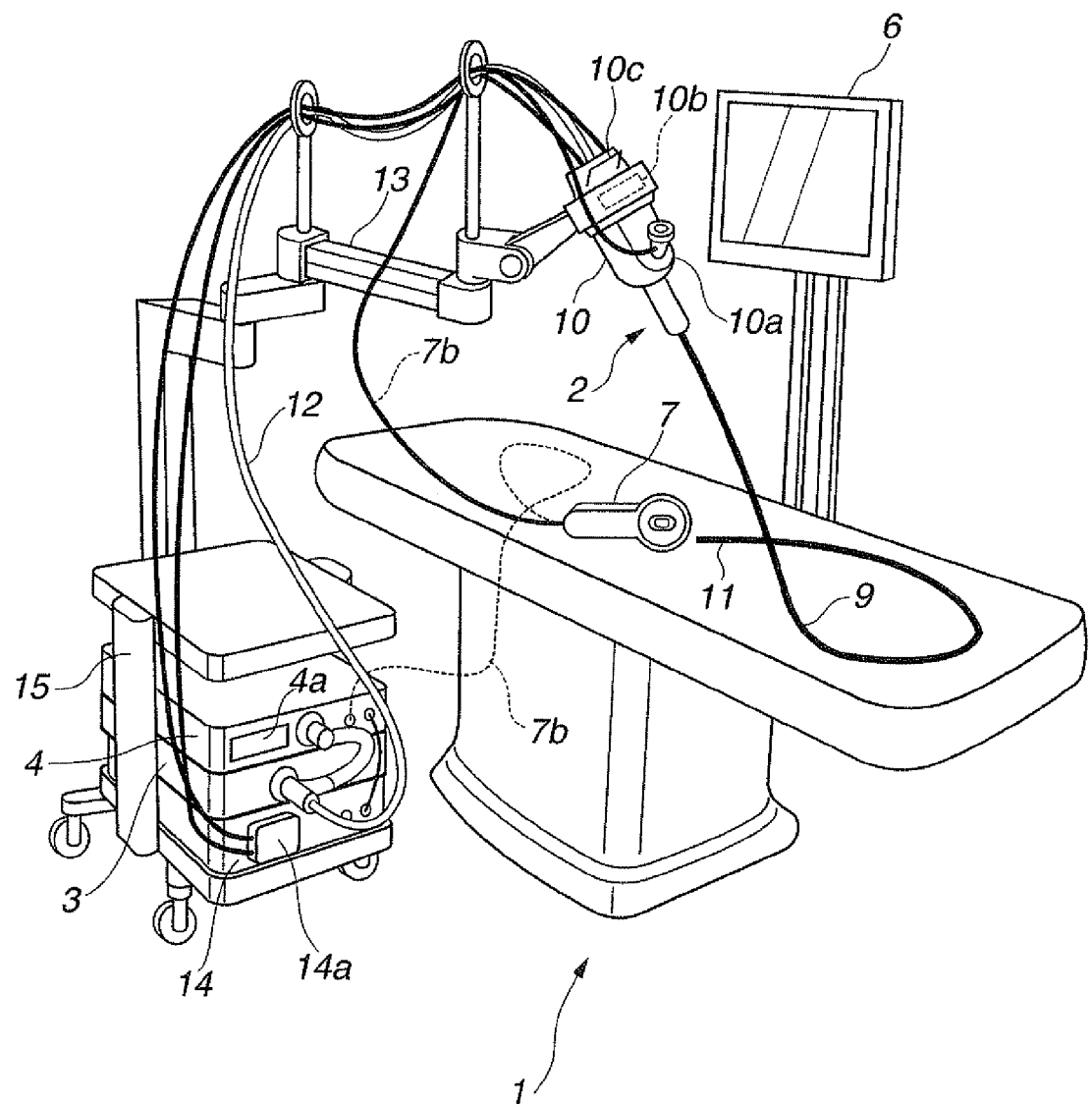
FIG. 1 is a diagram showing a configuration of an electric bending endoscope apparatus according to an embodiment 1 of the present invention.
Figure 2:
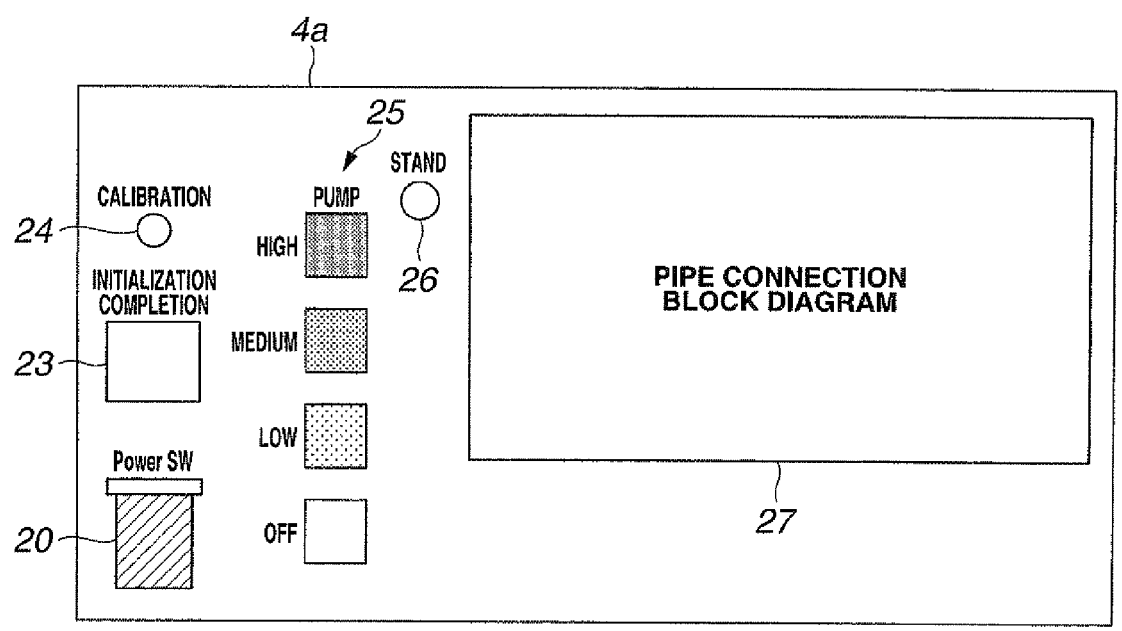
FIG. 2 is a diagram showing a configuration of a front panel of an image processing apparatus in FIG. 1.
Figure 3:
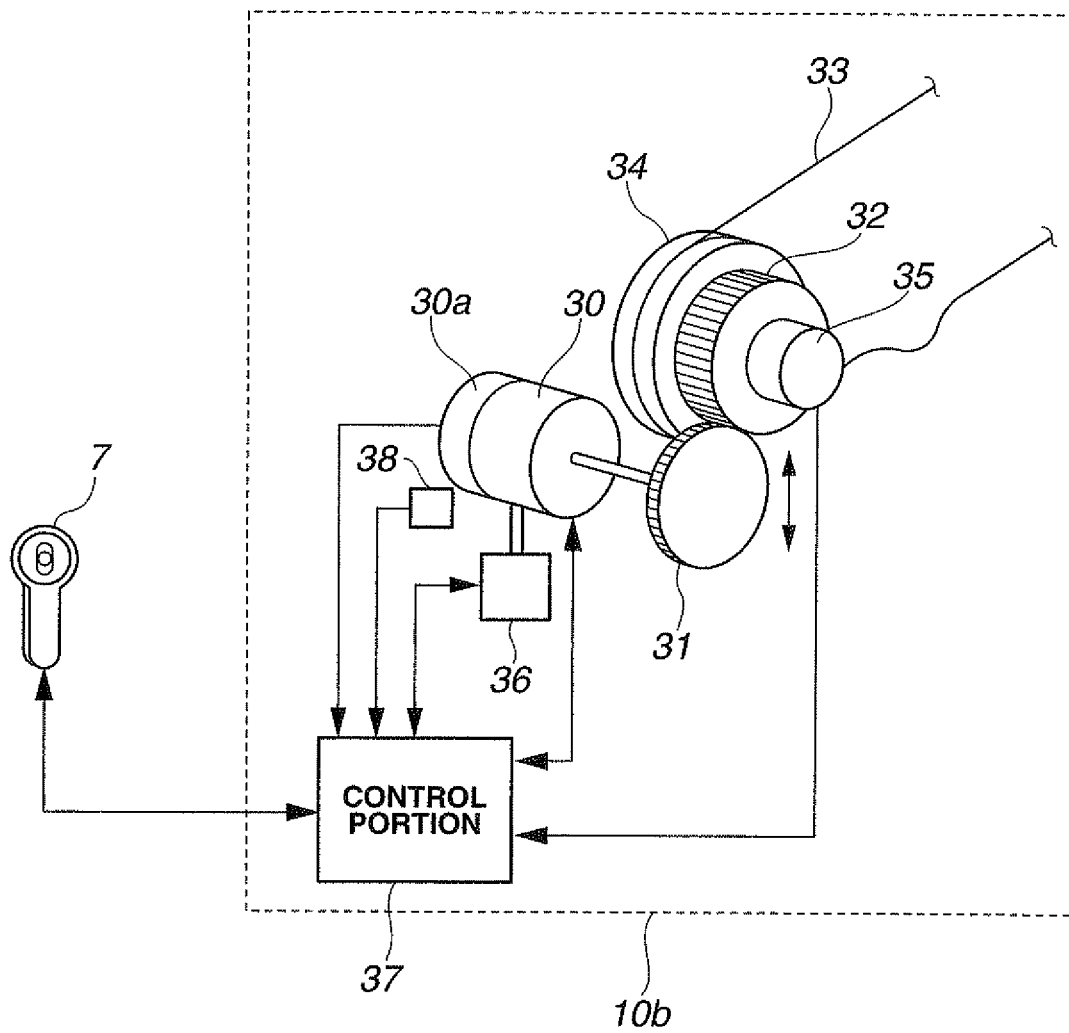
FIG. 3 is a diagram showing a configuration of a bending control portion in FIG. 1.
Figure 4:
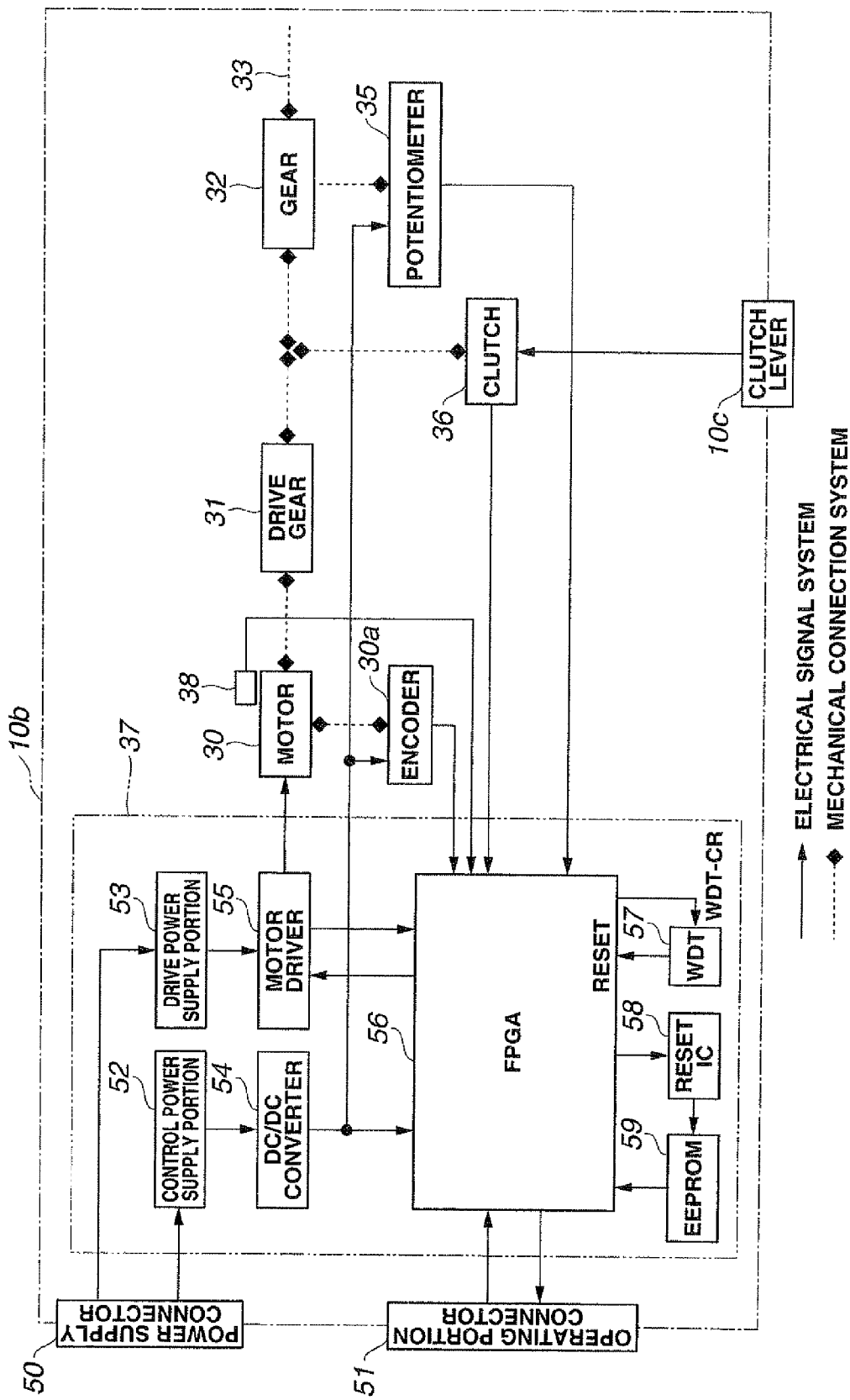
FIG. 4 is a diagram showing a configuration of a control portion of the bending control portion in FIG. 1.
Figure 5:
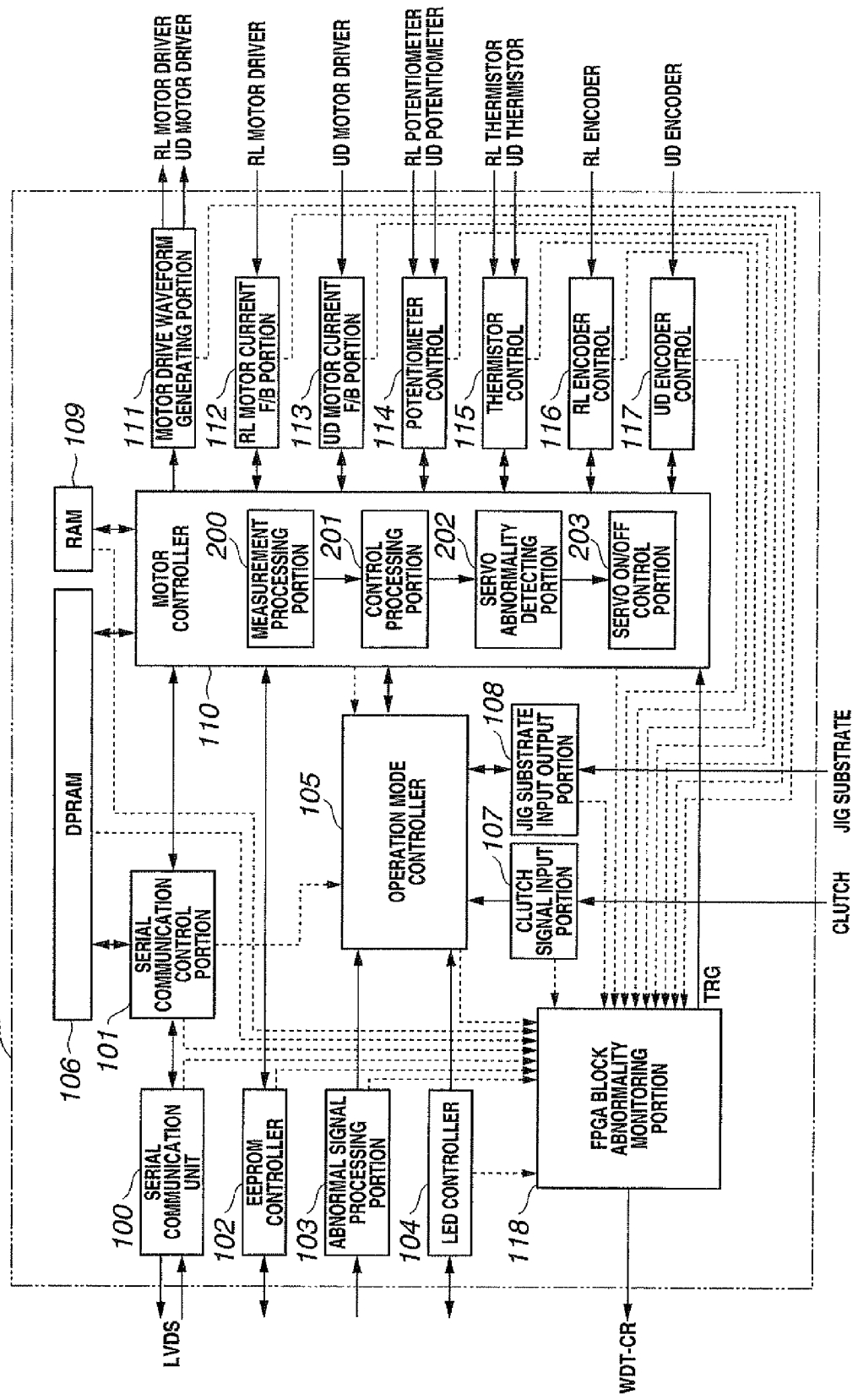
FIG. 5 is a diagram showing a configuration of logical blocks of an FPGA in FIG. 4.
Figure 6:
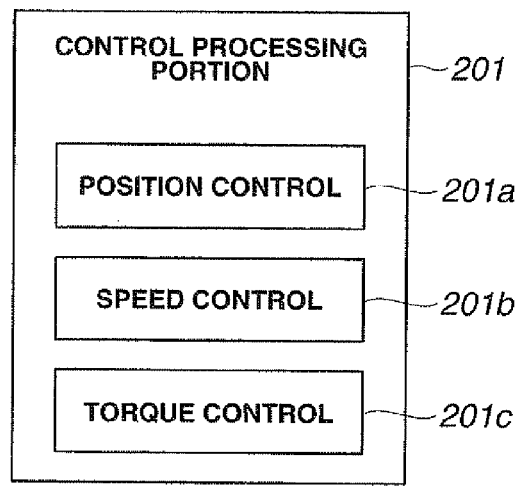
FIG. 6 is a diagram showing a configuration of a control processing portion of a motor controller in FIG. 5.
Figure 7:
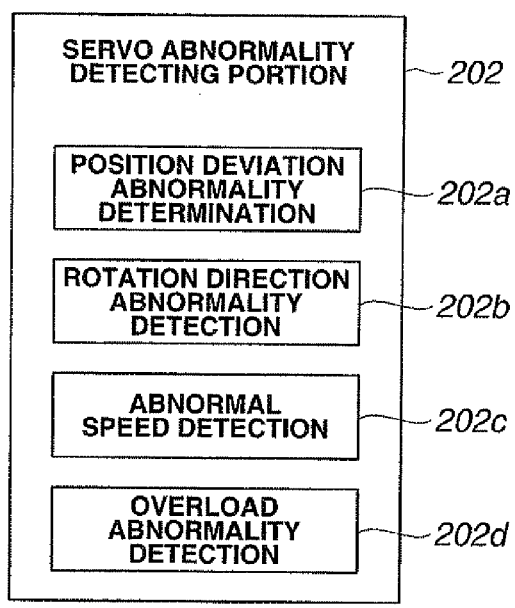
FIG. 7 is a diagram showing a configuration of a servo abnormality detecting portion of the motor controller in FIG. 5.
Figure 8:
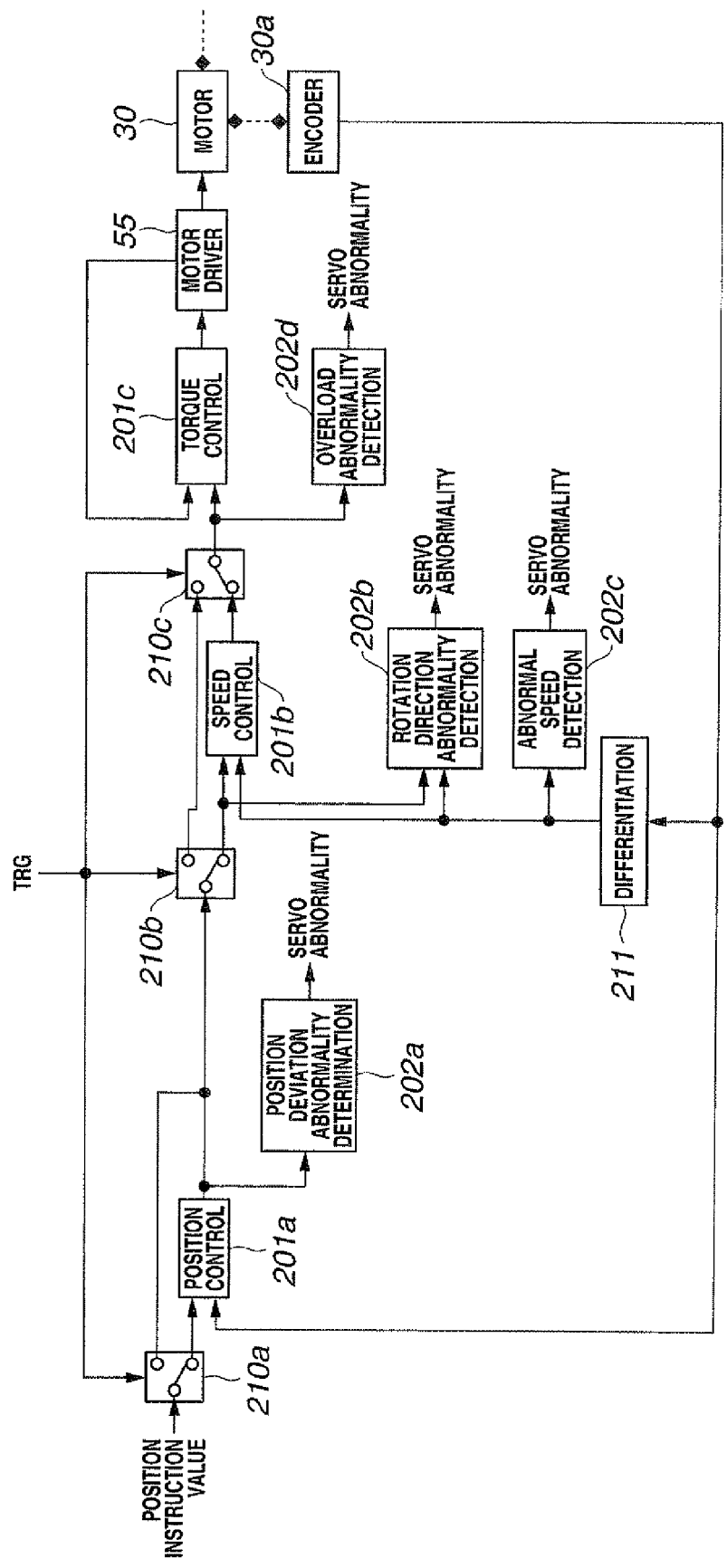
FIG. 8 is a first diagram explaining servo control in the motor controller in FIG. 5.
Figure 9:
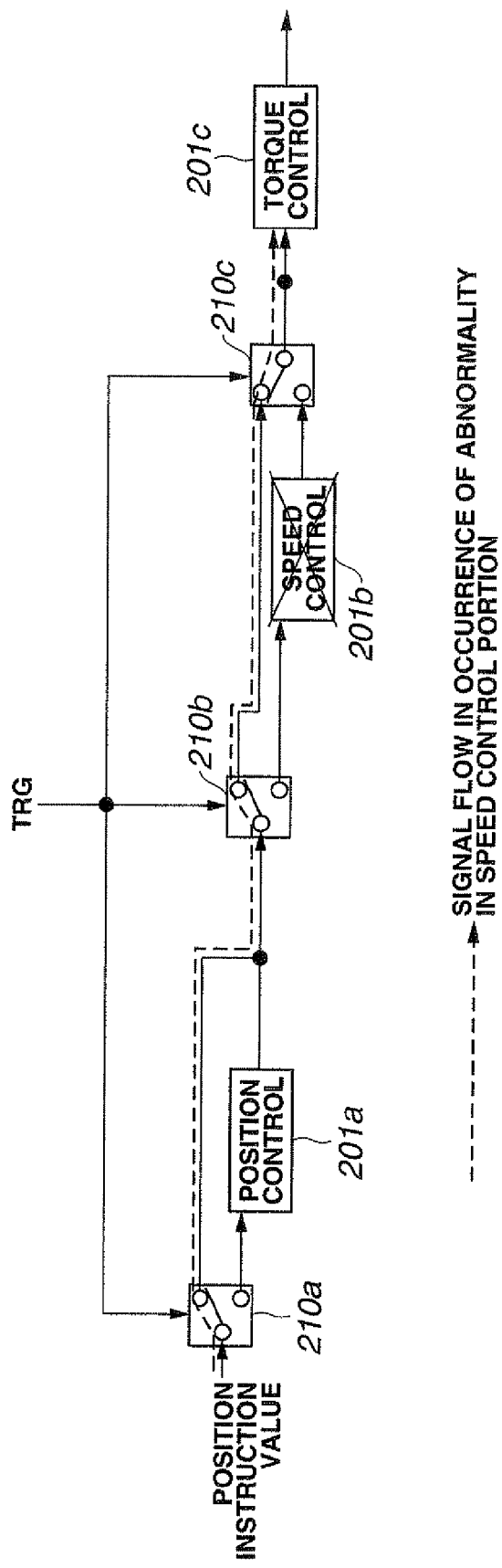
FIG. 9 is a second diagram explaining the servo control in the motor controller in FIG. 5.
Figure 10:
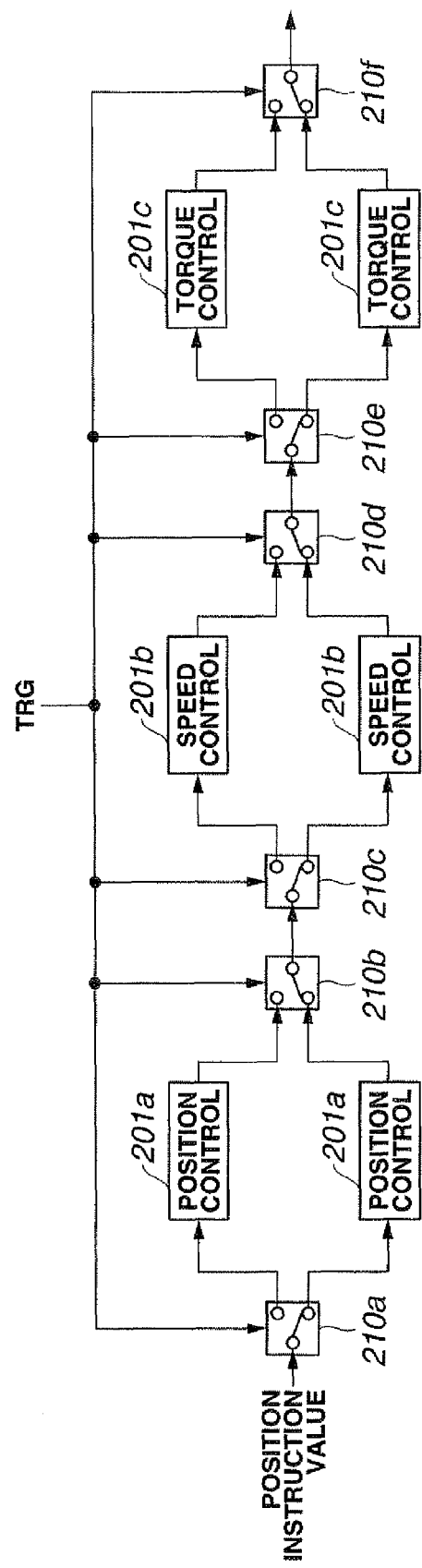
FIG. 10 is a diagram explaining a first modification of the servo control in the motor controller in FIG. 5.
Figure 11:
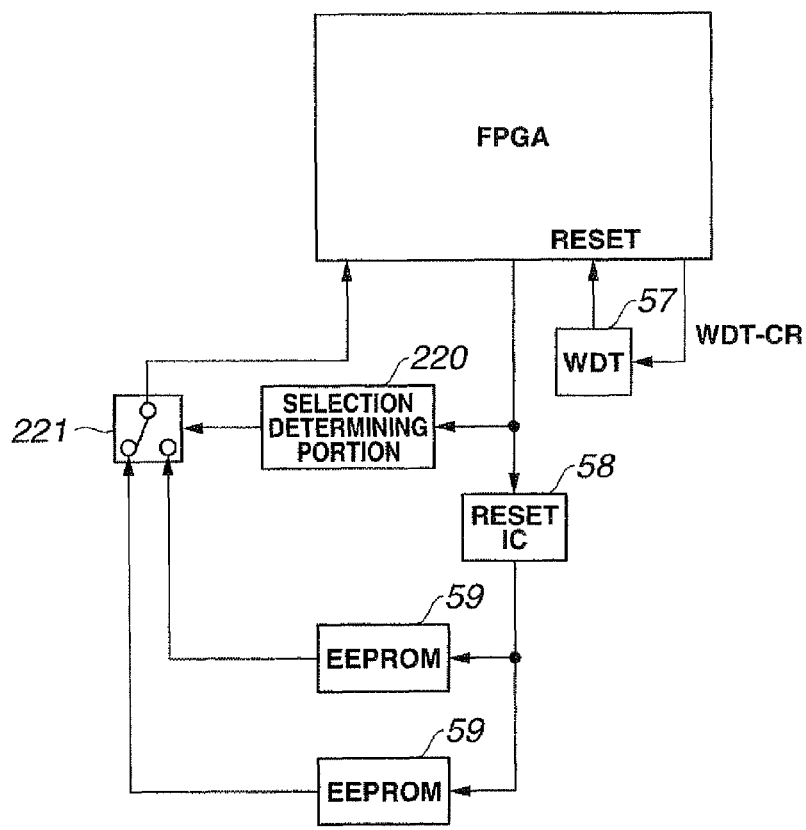
FIG. 11 is a diagram explaining a modification of the configuration of the FPGA in FIG. 4.
Figure 12:
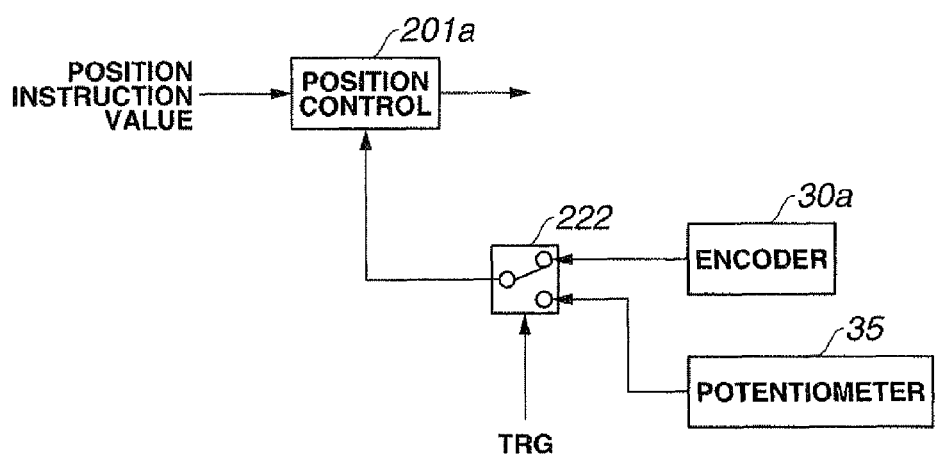
FIG. 12 is a diagram explaining a second modification of the servo control in the motor controller in FIG. 5.
Figure 13:
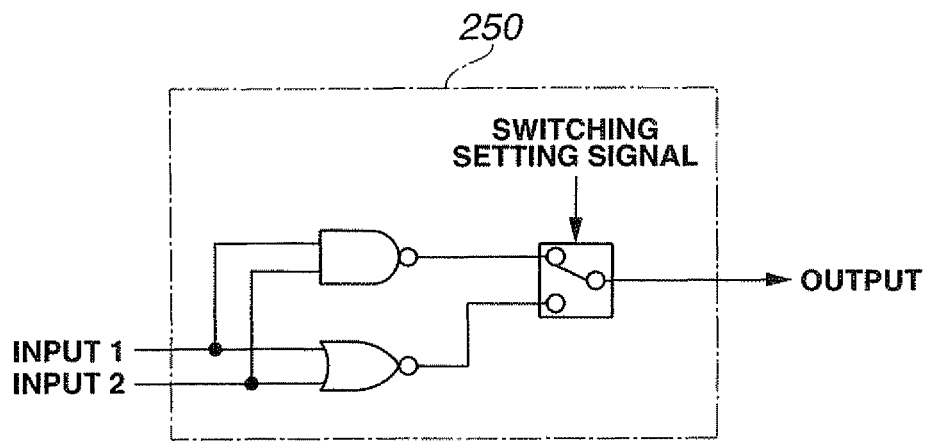
FIG. 13 is a first diagram explaining a logical element block configuring an FPGA block abnormality monitoring portion in FIG. 5.
Figure 14:
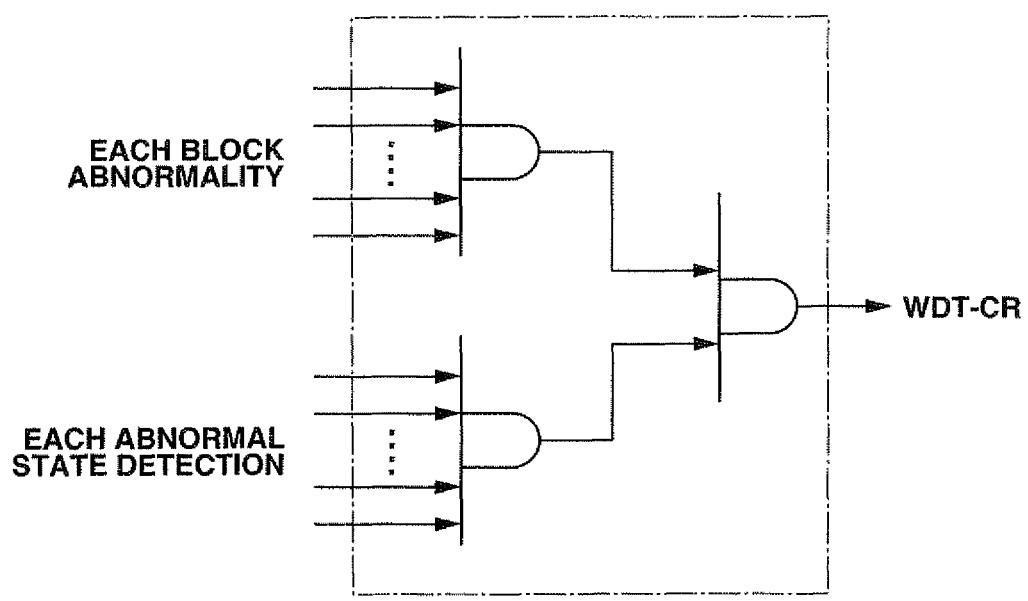
FIG. 14 is a second diagram explaining a logical element block configuring the FPGA block abnormality monitoring portion in FIG. 5.
Figure 15:
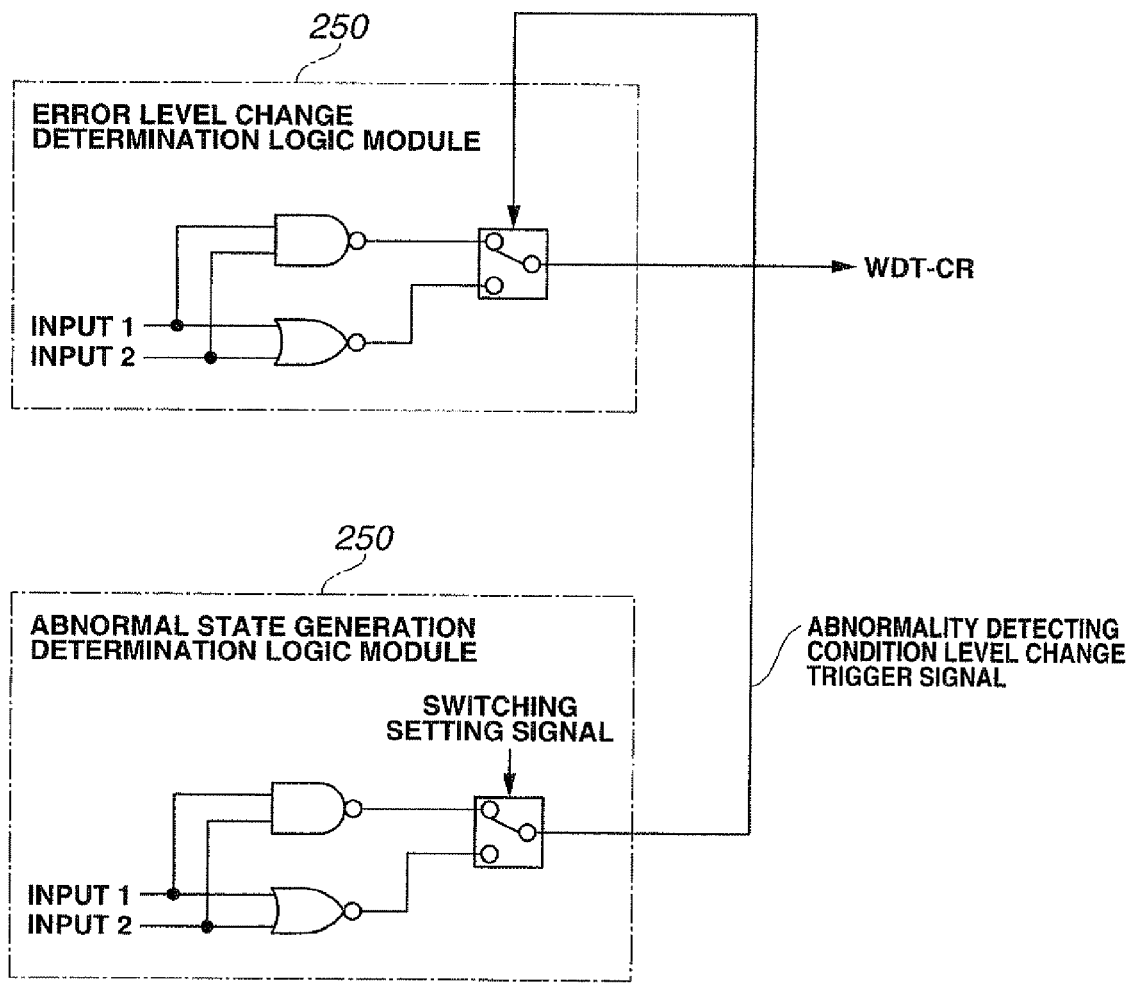
FIG. 15 is a first diagram explaining a logic determination block using the logical element blocks in FIG. 13.
Figure 16:
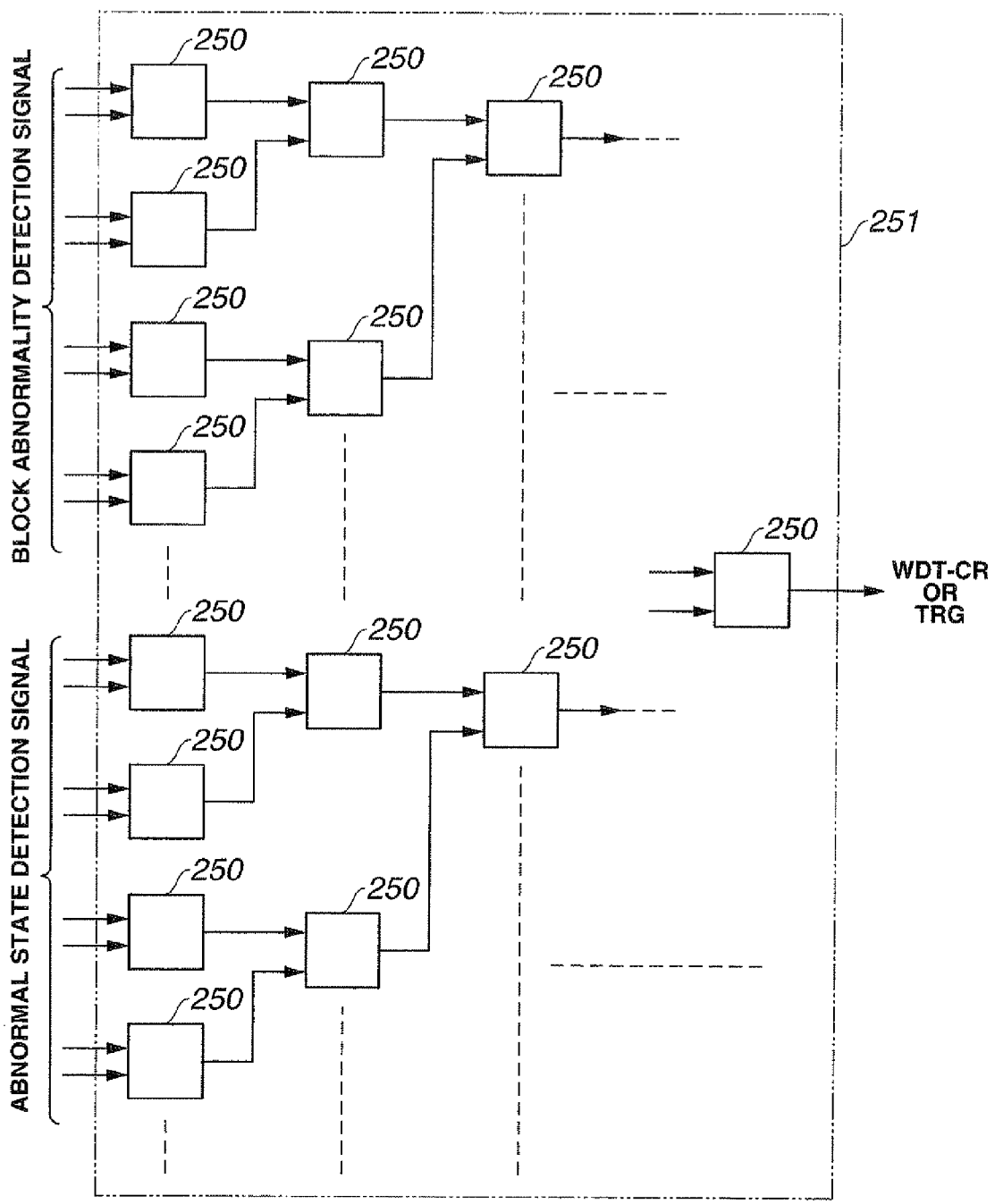
FIG. 16 is a second diagram explaining a logic determination block using the logical element blocks in FIG. 12.
Figure 17:
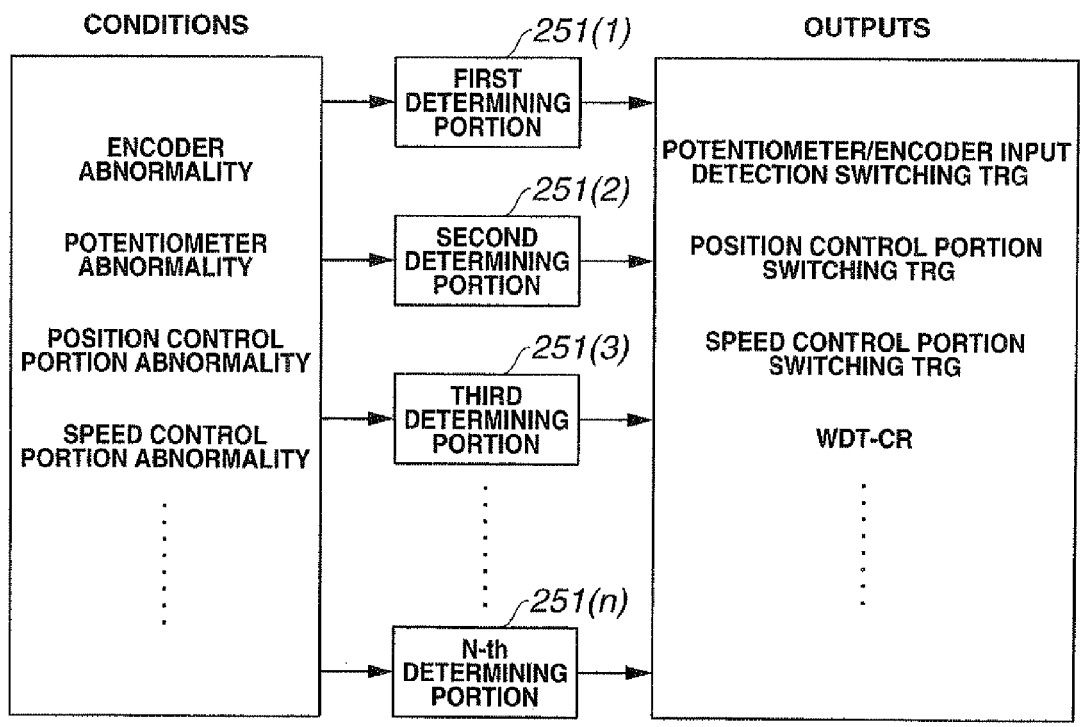
FIG. 17 is a third diagram explaining a logic determination block using the logical element blocks in FIG. 13.
Figure 18:
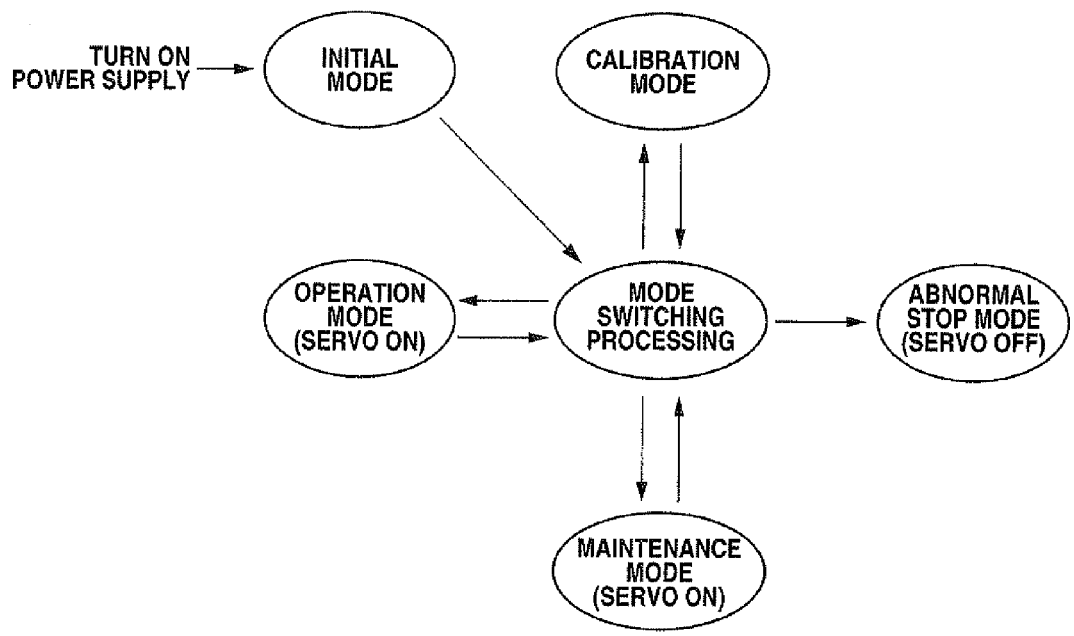
FIG. 18 is a diagram explaining the transition of processing in the FPGA in FIG. 5.
Figure 19:
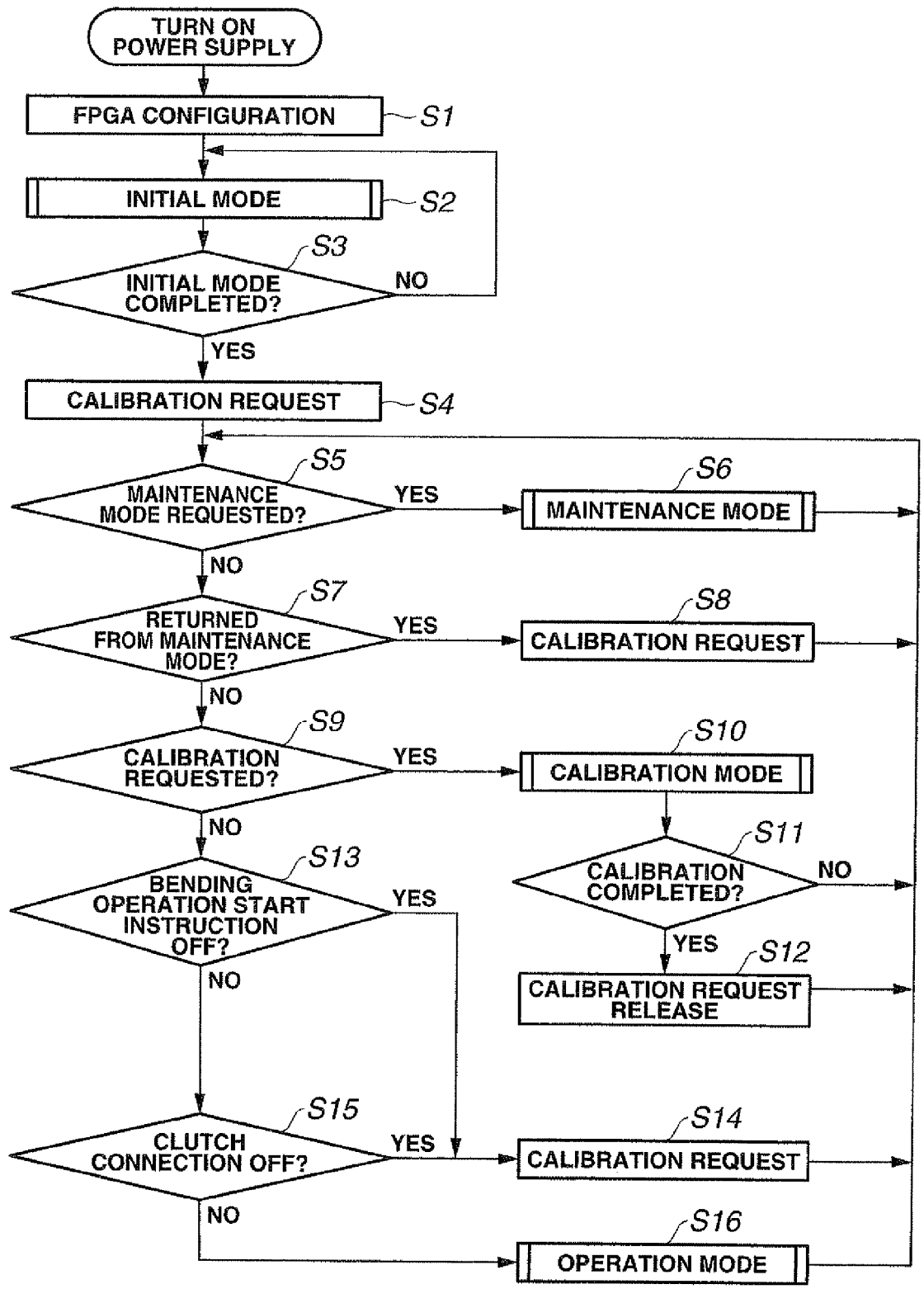
FIG. 19 is a flow chart explaining processing in the FPGA in FIG. 5.
Figure 20:
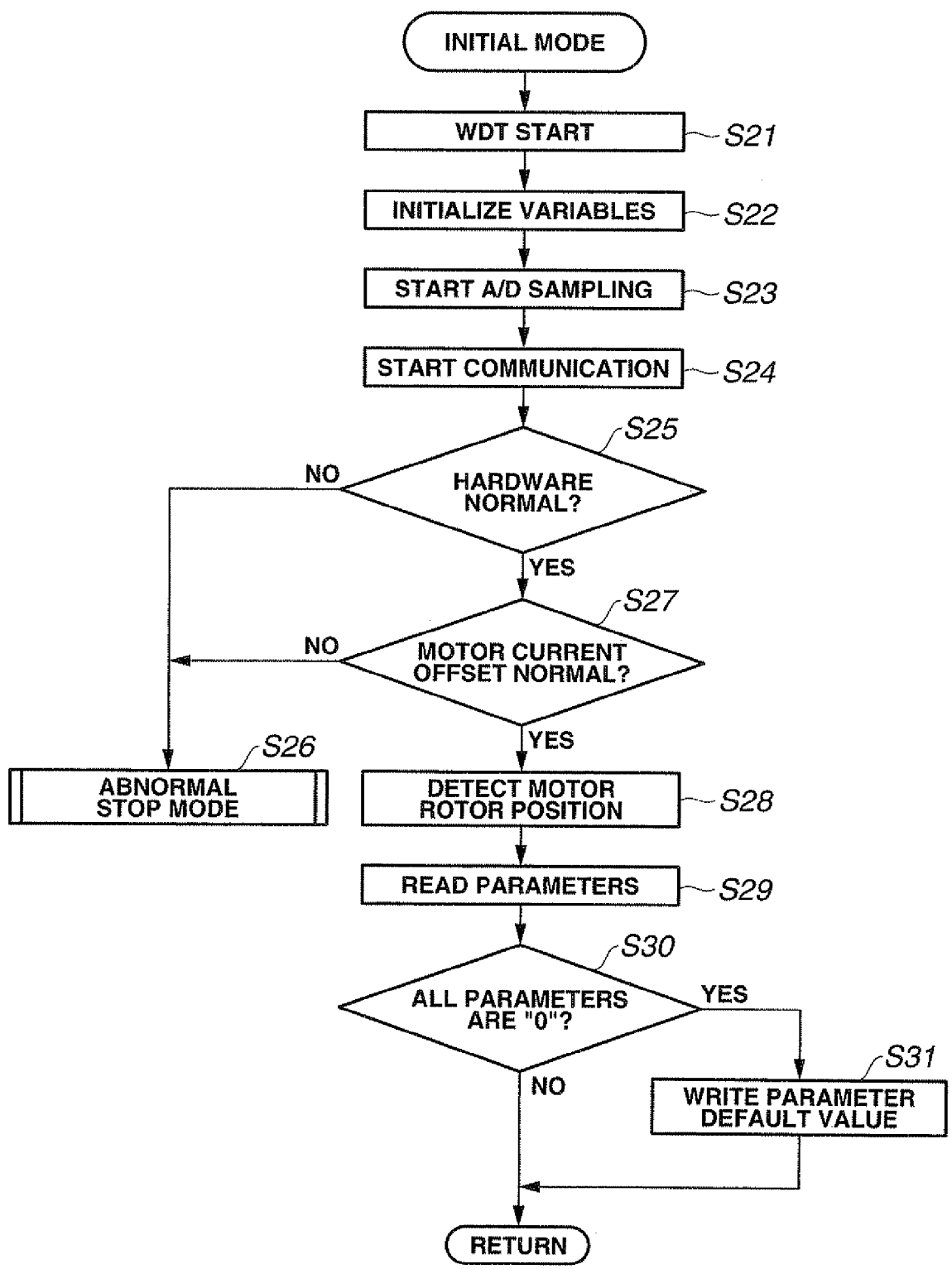
FIG. 20 is a flow chart explaining initial mode processing in FIG. 19.
Figure 21:
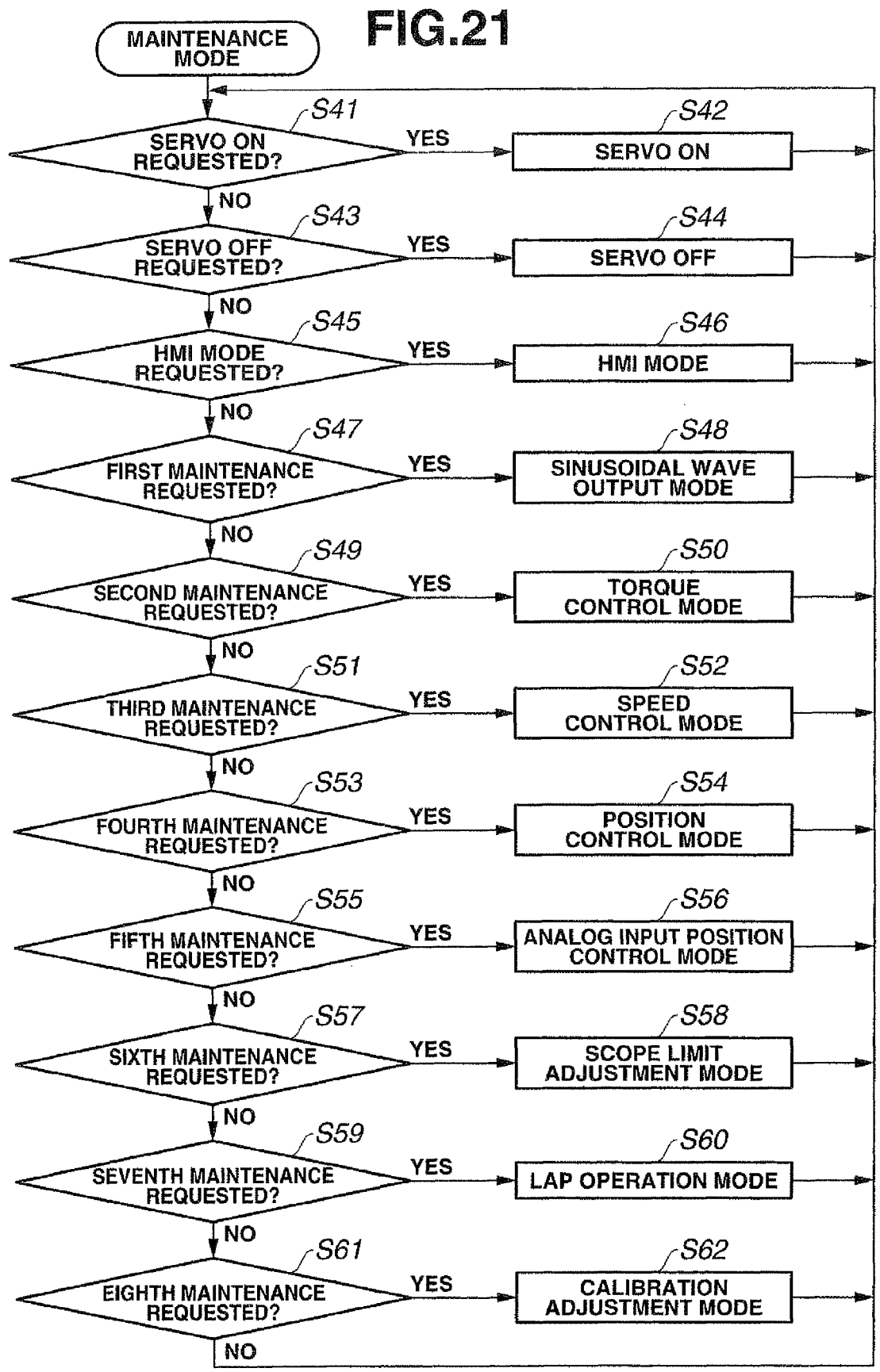
FIG. 21 is a flow chart explaining maintenance mode processing in FIG. 19.
Figure 22:
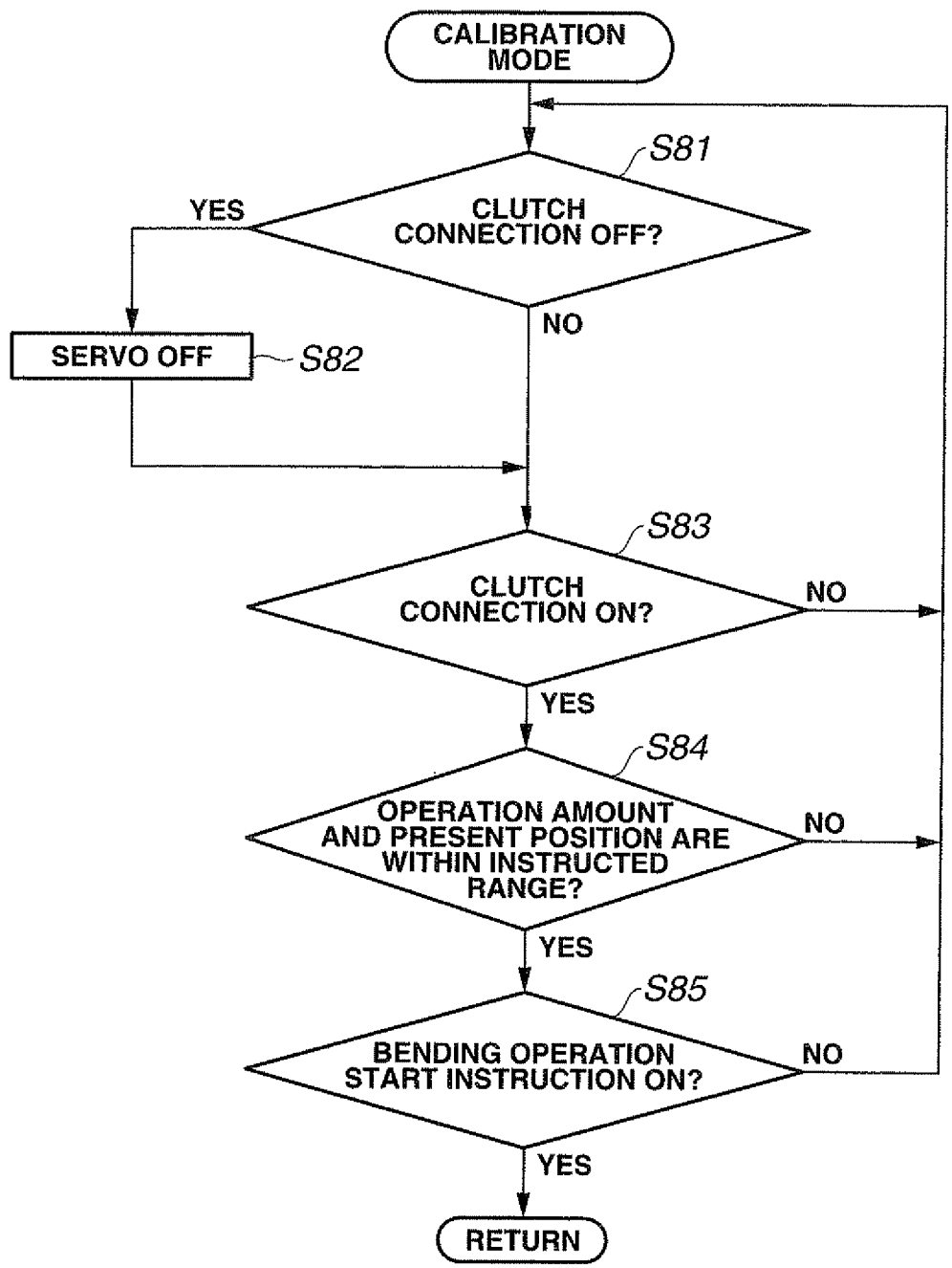
FIG. 22 is a flow chart explaining calibration mode processing in FIG. 19.
Figure 23:
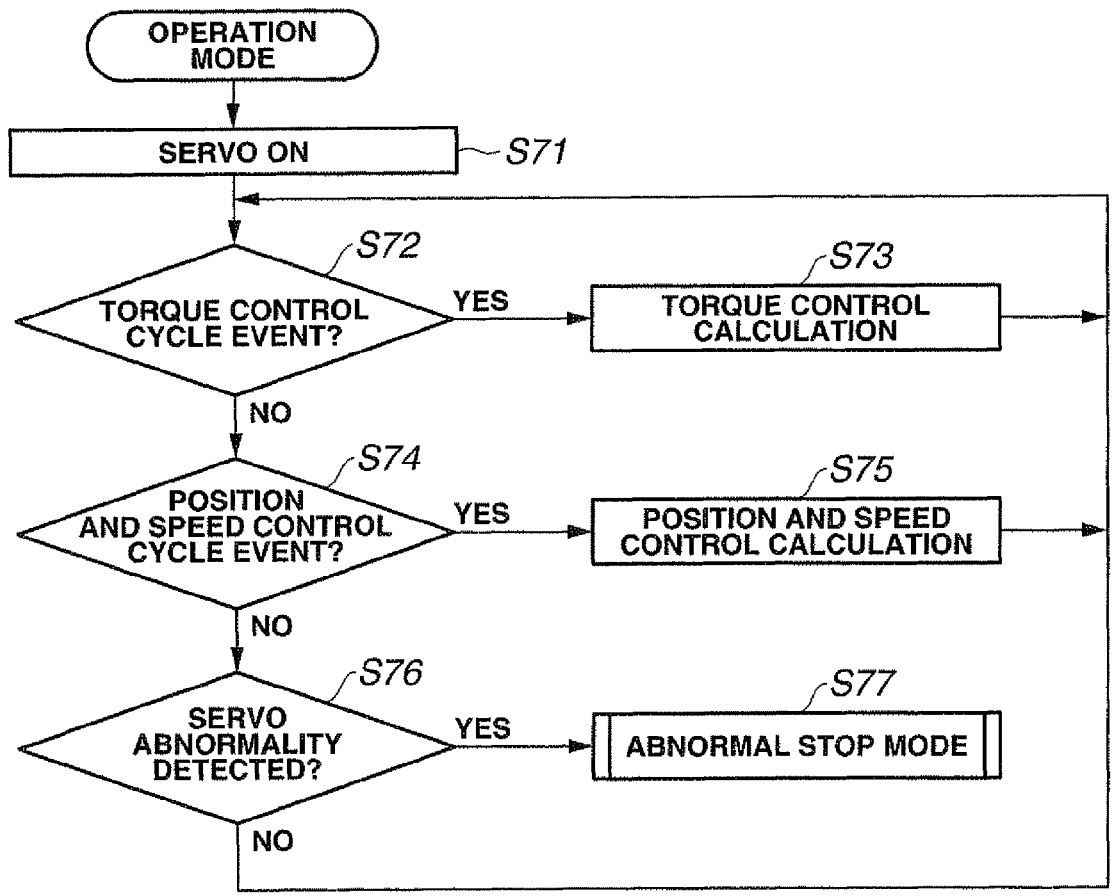
FIG. 23 is a flow chart explaining operation mode processing in FIG. 19.
Figure 24:
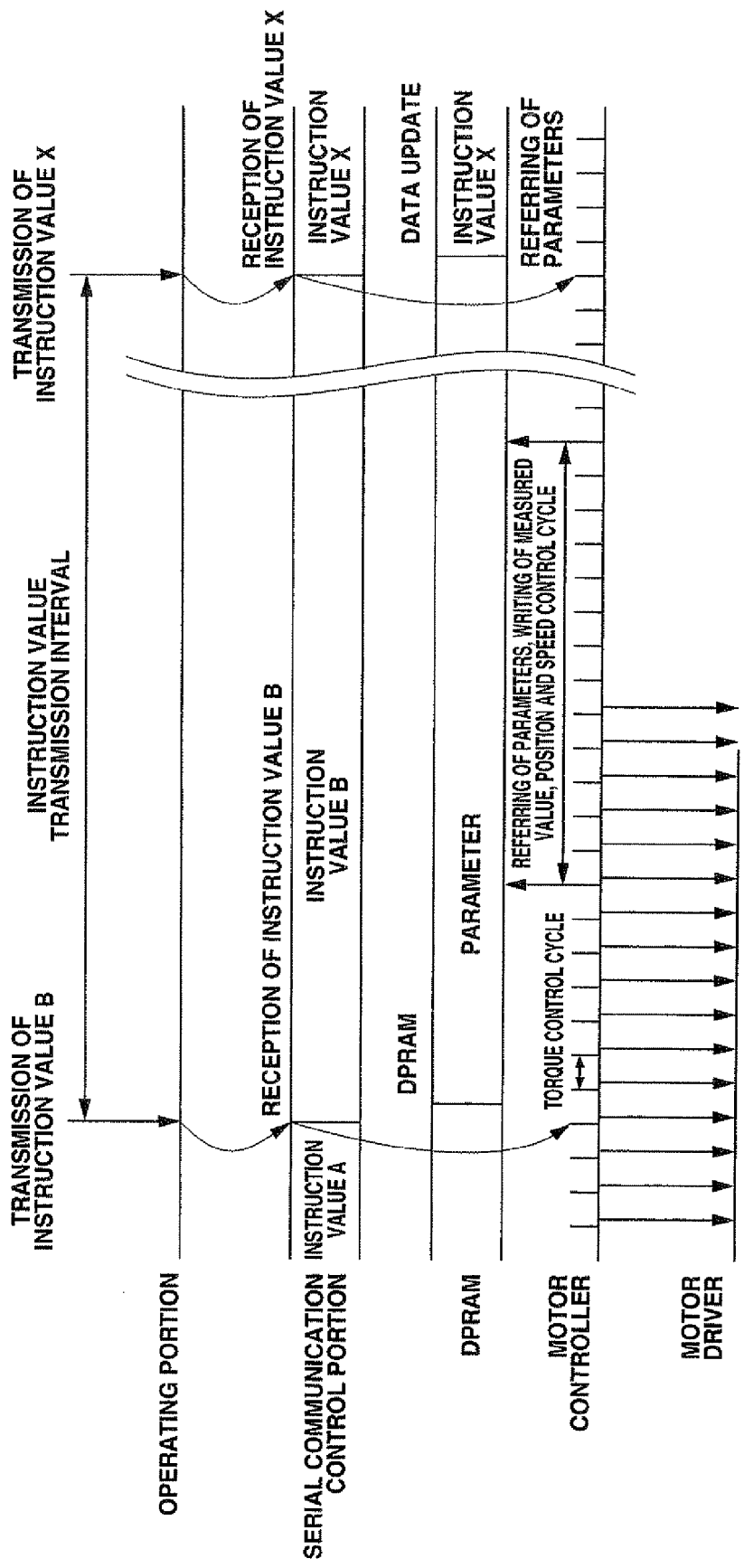
FIG. 24 is a timing chart explaining operation mode processing in FIG. 19.

FIG. 1 to FIG. 24 relate to an embodiment 1 according to the present invention. FIG. 1 is a diagram showing a configuration of an electric bending endoscope apparatus. FIG. 2 is a diagram showing a configuration of a front panel of an image processing apparatus in FIG. 1. FIG. 3 is a diagram showing a configuration of a bending control portion in FIG. 1. FIG. 4 is a diagram showing a configuration of a control portion of the bending control portion in FIG. 1. FIG. 5 is a diagram showing a configuration of a logical block of an FPGA in FIG. 4, FIG. 6 is a diagram showing a configuration of a control processing portion of a motor controller in FIG. 5. FIG. 7 is a diagram showing a configuration of a servo abnormality detecting portion of the motor controller in FIG. 5. FIG. 8 is a first diagram explaining servo control in the motor controller in FIG. 5. FIG. 9 is a second diagram explaining the servo control in the motor controller in FIG. 5. FIG. 10 is a diagram explaining a first modification of the servo control in the motor controller in FIG. 5. FIG. 11 is a diagram explaining a modification of the configuration of FPGA in FIG. 4. FIG. 12 is a diagram explaining a second modification of the servo control in the motor controller in FIG. 5. FIG. 13 is a first diagram explaining a logical element block configuring an FPGA block abnormality monitoring portion in FIG. 5. FIG. 14 is a second diagram explaining the logical element block configuring the FPGA block abnormality monitoring portion in FIG. 5. FIG. 15 is a first diagram explaining a logic determination block using the logical element blocks in FIG. 13. FIG. 16 is a second diagram explaining a logic determination block using the logical element blocks in FIG. 13. FIG. 17 is a third diagram explaining a logic determination block using the logical element blocks in FIG. 13. FIG. 18 is a diagram explaining the transition of processing in the FPGA in FIG. 5. FIG. 19 is a flow chart explaining processing in the FPGA in FIG. 5. FIG. 20 is a flow chart explaining initial mode processing in FIG. 19. FIG. 21 is a flow chart explaining maintenance mode processing in FIG. 19. FIG. 22 is a flow chart explaining calibration mode processing in FIG. 19. FIG. 23 is a flow chart explaining operation mode processing in FIG. 19. FIG. 24 is a timing chart explaining operation mode processing in FIG. 19.

In the conventional electric bending endoscope in which a microcomputer (for example, a CPU and a MPU) is usually used as a servo control portion for performing the motor control of the bending control portion and serves as a calculating portion for controlling the response speed of the motor, there is a problem that since a sequential processing is performed in the microcomputer, when a part of the processing functions stop, all the functions stop, so as to cause a trouble in the bending operation, and thereby the examination as a whole is made complicated.

The present embodiment has been made in view of the above described circumstances. An object of the present embodiment is to provide an electric bending endoscope which is capable of, even when a trouble is caused in a part of the function of the bending control portion, continuing the bending operation.

As shown in FIG. 1, an electric bending endoscope apparatus 1 according to the present embodiment incorporates an image pickup device (not shown) in a distal end rigid portion of an endoscope insertion portion (hereinafter abbreviated as insertion portion) 9, and is mainly configured by including: an electric bending endoscope (hereinafter abbreviated as endoscope) 2 in which a bending portion 11 of the insertion portion 9 is bent by electrically pulling a bending wire (as will be described below) configuring bending drive unit; a remote control operation portion 7 as instruction unit which performs a drive operation of the bending portion 11, and the like; an image processing apparatus 4 which generates a video signal from an image signal transmitted via a universal cable 12; a light source apparatus 3 which supplies illumination light to an illumination optical system (not shown) via a light guide fiber bundle (not shown) incorporated in the universal cable 12; a monitor 6, as a display apparatus, to which the video signal generated in the image processing apparatus 4 is outputted, and which displays the video signal as an endoscopic image; air and water supply pipes; and a pump unit 14 which performs a suction operation.

The light source apparatus 3, the image processing apparatus 4, and the pump unit 14 are mounted on a cart 15. A flow rate control cassette 14a having a mechanism for adjusting the flow rate in the air and water supply pipes and the flow rate in the suction operation is detachably provided in the pump unit 14. Further, it is configured such that an endoscope fixing arm 13 which holds and fixes the endoscope 2 is provided in the cart 15, and that a proximal end grasping portion 10 of the endoscope 2 is detachably held and fixed to the distal end of the endoscope fixing arm 13.

It is configured such that a forceps plug 10a to which a suction tube from the flow rate control cassette 14a can be connected is arranged in the proximal end grasping portion 10 of the endoscope 2, and that the universal cable 12 and the air and water supply tubes from the flow rate control cassette 14a are connected to the proximal end grasping portion 10 of the endoscope 2. The air and water supply tubes and the like, and the suction tube are connected to, for example, an air supply pipe, a water supply pipe and a suction pipe (all not shown) in the insertion portion 9.

Further, a bending control portion 10b which controls a motor, and the like, to electrically drive the bending portion 11, is incorporated in the proximal end grasping portion 10. The remote control operation portion 7 is connected to the bending control portion 10b via a cable 7b. Note that the remote control operation portion 7 is also configured so as to be able to be connected to the image processing apparatus 4 via the cable 7b, and to be able to be connected to the bending control portion 10b via the universal cable 12.

The remote control operation portion 7 includes, although not shown, for example, a joystick which is an operation input device for performing an electric bending operation of the bending portion 11, an operation input switch for the air and water supply operation and the suction operation, and a scope switch having a remote switch for freeze and release operations, and the like, in the image processing apparatus 4. The image processing apparatus 4 serving as bending state detecting unit and bending operation control unit is configured to be able to be connected to the pump unit 14. A front panel 4a of the image processing apparatus 4 is configured by including, as shown in FIG. 2, a power switch 20, an initialization button 23 having an LED function to instruct the initialization of the electric bending endoscope apparatus 1 and to notify the completion of initialization, a calibration LED portion 24 configured to notify the calibration of the electric bending of the bending portion 11, an operation input switch group 25 for the air and water supply operation and the suction operation of the pump unit 14, an examination possible LED 26 configured to notify a state in which the examination by the electric bending endoscope apparatus 1 can be performed, a pipe connection display portion 27 configured to display connection states of the air supply pipe, the water supply pipe, and the suction pipe, and the like.

As shown in FIG. 3, a vertical bending wire 33 and a lateral bending wire (not shown) which are extended from the bending control portion 10b and which are used for bending the bending portion 11, are inserted into the insertion portion 9. Note that in the following description, a configuration relating to the vertical bending wire 33 will be described, and a configuration relating to the lateral bending wire, which configuration is the same as the configuration of the vertical bending wire 33, is not shown for the sake of simplicity and the explanation thereof is also omitted.

The both end portions of the bending wire 33 is connected and fixed to a chain (not shown), which is arranged in mesh with a rotatable vertical sprocket portion 34 configuring the bending drive unit. Thereby, when the sprocket portion 34 is rotated in a predetermined direction, the bending wire 33 fixed to the chain is pulled, so as to make the bending portion 11 bent in a predetermined direction.

The sprocket portion 34 is arranged, for example, in the bending control portion 10b. The sprocket portion 34 includes a plurality of gears 31 and 32, which transmit the drive power of a bending motor 30 including a three phase motor, for example, as the vertical bending power unit, and a clutch mechanism portion 36, as drive power transmission disconnection and recovering unit, configured to make the gears engaged and disengaged to and from each other, for example. When the bending wire 33 is put in a state free of tension by the clutch mechanism portion 36, the bending portion 11 is put in a bending free state where the bending portion 11 can be freely bent by an external force.

Note that the bending drive unit is configured by the gears 31 and 32, the bending wire 33, the sprocket portion 34, the clutch mechanism portion 36, and the like.

The clutch mechanism portion 36 is configured to be switched between a drive power transmission disconnected state where the clutch mechanism portion 36 is disconnected, and a drive power transmission recovered state where the clutch mechanism portion 36 is connected, by switching a switching operation lever 10c (see FIG. 1), as state switching unit, to a drive power transmission disconnecting position (hereinafter referred to as bending free instruction position) or to a drive power transmission recovering position (hereinafter referred to as angle operation instruction position).

That is, the bending motor 30 and the sprocket portion 34 can be reversibly engaged and disengaged with and from each other by mechanically switching the clutch mechanism portion 36 to the disconnected state or the connected state by the switching operation of the switching operation lever 10c.

The rotation amount of the sprocket portion 34 is detected by a potentiometer 35 which is bending angle detecting unit. Note that reference character 30a denotes an encoder which detects the rotation amount of the bending motor 30. Further, reference numeral 38 denotes a thermistor which measures the temperature of the bending motor 30. The bending state detecting unit is configured by the potentiometer 35 or the encoder 30a.

The remote control operation portion 7, the encoder 30a, the potentiometer 35, the clutch mechanism portion 36, and the thermistor 38 are connected to a control portion 37 of the bending control portion 10b.

In the bending control portion 10b, as shown in FIG. 4, there are provided a power supply connector 50 to which a power supply cable (not shown) is connected via the universal cable 12, and an operation portion connector 51 to which the cable 7a of the remote control operation portion 7 is connected. The power supply connector 50 is connected to a control power supply portion 52 and a drive power supply portion 53 in the control portion 37. The control power supply portion 52 is configured so as to supply the control power to each portion via a DC/DC converter 54. Further, the drive power supply portion 53 supplies the drive power so as to enable a motor driver 55 to generate three phase sinusoidal wave power.

The operation portion connector 51 is connected to an FPGA (field programmable gate array) 56 as bending operation control unit in the bending control portion 10b. The FPGA 56 performs configuration based on data stored in an EEPROM 59 so that internal cells of the FPGA 56 are configured into desired logical blocks. The encoder 30a, the potentiometer 35, the clutch mechanism portion 36, and the thermistor 38 are connected to the FPGA 56, so as to be controlled by the FPGA 56. Further, the FPGA 56 supplies data for generating the three phase sinusoidal wave power to the motor driver 55, and thereby the motor driver 55 supplies the three phase sinusoidal wave power to the bending motor 30.

The FPGA 56 outputs a WDT-CR signal which clears a WDT (watchdog timer) 57, when an abnormality larger than a predetermined fixed level is caused in the internal cell. On the basis of the WDT-CR signal, a reset signal is outputted to the FPGA 56 from the WDT 57, so that the FPGA 56 is resets. It is configured such that when receiving the reset signal, the FPGA 56 starts a reset IC 58, and reconfigures the logical block of the internal cell on the basis of the data in the EEPROM 59.

As shown in FIG. 5, the logical block of the FPGA 56 is configured by a serial communication unit 100, a serial communication control portion 101, an EEPROM controller 102, an abnormal signal processing portion 103, an LED controller 104, an operation mode controller 105, a DPRAM 106, a clutch signal input portion 107, a jig substrate input output portion 108, a RAM 109, a motor controller 110, a motor drive waveform generating portion 111, an RL (right and left) motor current F/B portion 112, a UD (up and down) motor current F/B portion 113, a potentiometer control portion 114, a thermistor control portion 115, an RL encoder control portion 116, a UD encoder control portion 117, and an FPGA block abnormality monitoring portion 118. Further, the motor controller 110 is configured by including respective logical blocks of a measurement processing portion 200, a control processing portion 201, a servo abnormality detecting portion 202, and a servo ON/OFF control portion 203.

Note that in FIG. 5, solid lines represent a flow of normal control and data signals, and broken lines represent a flow of a logical block abnormal signal, a servo abnormal signal, or a communication abnormal signal.

The serial communication unit 100 performs serial communication with the remote control operation portion 7 by, for example, an LVDS, or the like. The serial communication control portion 101 controls the serial communication unit 100, and communicates with the motor controller 110 to store data received from the motor controller 110 in the DPRAM 106.

The EEPROM controller 102 performs configuration of the FPGA 56 according to a program stored in the EEPROM 59.

The abnormal signal processing portion 103 monitors abnormality in the power supply voltage and overcurrent of the bending motor 30, and outputs a monitoring result to the operation mode controller 105.

The clutch signal input portion 107 receives a state signal representing the power transmission disconnected state or the drive power transmission recovered state from the clutch mechanism portion 36, and outputs the state signal to the operation mode controller 105.

The jig substrate input output portion 108 transmits and receives data for performing debug processing to and from a jig substrate (not shown). Further, the LED controller 104 controls an LED of the jig substrate.

The operation mode controller 105 outputs to the motor controller 110 an operation mode which corresponds to the power transmission disconnected state or the drive power transmission recovered state of the clutch mechanism portion 36, and which corresponds to the connection state with the jig substrate. Note that the operation mode controller 105 is configured to receive a communication abnormal signal from the serial communication control portion 101, and a servo abnormal signal from the motor controller 110, and to thereby output an operation mode based on the abnormal signals to the motor controller 110.

Further, the motor drive waveform generating portion 111 reads sinusoidal wave data stored in the RAM 109 via the motor controller 110 to generate three phase sinusoidal wave data, and outputs the three phase sinusoidal wave data to the RL (right and left) motor driver and the UD (up and down) motor driver 55.

The RL (right and left) motor current F/B portion 112 converts the U phase current value and the V phase current value from the RL (right and left) motor into digital signals, and outputs the digital signals to the motor controller 10. Similarly, the UD (up and down) motor current F/B portion 113 converts the U phase current value and the V phase current value from the UD (up and down) motor 30 into digital signals, and outputs the digital signals to the motor controller 110.

The potentiometer control portion 114 converts the position information on the potentiometer 35 connected to the RL (right and left) sprocket portion and the UD (up and down) sprocket portion 34 into digital signals, and outputs the digital signals to the motor controller 110.

The thermistor control portion 115 converts temperature data measured by the thermistor 38 provided in the RL (right and left) motor and the UD (up and down) motor 30 into digital signals, and outputs the digital signals to the motor controller 110.

The RL encoder control portion 116 and the UD encoder control portion 117 output count values of the encoder 30a provided in the RL (right and left) motor and the UD (up and down) motor 30 to the motor controller 110.

Then, the motor controller 110 performs the servo control of the RL (right and left) motor and the UD (up and down) motor 30 on the basis of the operation mode by using the measurement processing portion 200, the control processing portion 201, the servo abnormality detecting portion 202, and the servo ON/OFF control portion 203.

Further, the FPGA block abnormality monitoring portion 118 is configured to receive the logical block abnormal signal of each of the above described logical blocks, the servo abnormal signal, or the communication abnormal signal, and is configured, on the basis of the abnormal signals, to output the TRG signal to the motor controller 10, and to output the WDT-CR to the WDT 57.

Here, as shown in FIG. 6, the control processing portion 201 of the motor controller 110 is configured by including a position control block 201a, a speed control block 201b, and a torque control block 201c. Further, as shown in FIG. 7, the servo abnormality detecting portion 202 is configured by including a position deviation abnormality determining block 202a, a rotation direction abnormality detecting block 202b, an abnormal speed detecting block 202c, and an overload abnormality detecting block 202d.

Next, the servo control in the motor controller 110 will be described with reference to FIG. 8. The position control block 201a compares a position instruction value from the remote control operation portion 7 with an output value of the encoder 30a. When the position deviation exceeds a predetermined value, the position deviation abnormality determining block 202a outputs a servo abnormal signal.

Further, the speed control block 201b compares the output of the position control block 201a with a differential value (differentiated in a differential circuit 211) of the output value of the encoder 30a. The rotation direction abnormality detecting block 202b outputs a servo abnormal signal, when detecting an abnormality in the rotation direction on the basis of the output of the position control block 201a and the differential value of the output value of the encoder 30a. Further, the abnormal speed detecting block 202c outputs a servo abnormal signal, when detecting a speed abnormality on the basis of the differential value of the output value of the encoder 30a.

Further, the torque control block 201c controls the motor driver 55 by comparing the output of the speed control block 201b with the current value of the motor driver 55. The overload abnormality detecting block 202d monitors the load state of the bending motor 30 on the basis of the output of the speed control block 201b, and outputs a servo abnormal signal when determining the load state as an overload state.

An operation example at the time when there is an abnormality in the control loop, is described with reference to FIG. 9. Here, for the sake of simplicity, the F/B (feedback) configuration is omitted.

For example, the content in the case where there is a speed abnormality in the speed control block 201b is described. This represents the case where a position control instruction value is directly switched so as to be inputted into the current control portion (torque control block 201c). As indicated by the mark x in the diagram, when the speed control block 201b becomes inoperable, a signal generated by the abnormality determining portion (as will be described below) is inputted into the switching SWs (a switch portion 210a, a switch portion 210b, and switch portion 210c) via the TRG, so that the position control instruction value is directly inputted into the current control portion by switching the switching SWs (the data flow shown by the broken-line arrow in the diagram).

At this time, the loop gain constant set beforehand is also changed with absence of the speed control block 201b, and hence the gain setting value in the state where the speed control block 201b is absent is set again (is set to the value set beforehand for the state where the speed control does not exist).

Specifically, when the speed control gain setting value is set to "Sp" (Sp>0), and when the switching SWs are switched, it is clear that the closed loop characteristic is changed, from the fact that the gain setting value becomes "1" in the case where the speed control block 201b does not exist.

Thus, the closed loop characteristic is made to remain the same as much as possible, by such a way that only the speed control block 201b is removed from the circuit system by switching the switch portion 210b and the switch portion 210c without switching the other control portion, for example, the switch portion 210a, and that the gain of the position control block 201a is increased by the reduced amount of the closed loop gain which is reduced to Sp->1.

However, a dynamic filter is usually inserted in the speed control block 201b, and hence only a static gain is obtained when the speed control block 201b is absent. Thus, the dynamic characteristic cannot be changed. When it is desired to keep the dynamic characteristic similarly the same, this can be effected by using the configuration as shown in FIG. 11 or FIG. 11.

FIG. 10 shows an example in which when the FPGA 56 has an enough capacity, the speed control block 201b is switched to a speed control block which is arranged beforehand on the cell of the FPGA 56 in parallel with the speed control block 201b.

In the example shown in FIG. 10, there is adopted a system configured such that same two components are arranged, that when an abnormality occurs, the data flow between the respective control blocks is switched by using the switching SWs (switch portion 210a, switch portion 210b, switch portion 210c, switch portion 210d, switch portion 210e, and switch portion 210f) according to the TRG generated by the abnormality determining portion.

In the example of FIG. 11, there is shown a configuration example in which two EEPROMs 59 with the configuration program of the FPGA 56 stored therein beforehand are prepared so as to cope with a case where an error occurs in a part in the FPGA 56.

In the configuration shown in FIG. 11, a signal is outputted to a selection determining portion 220 from the FPGA 56 via an error status line, and a reconfiguration of the FPGA code is performed. It is configured such that either the program data of the first EEPROM 59 or the separately prepared program data of the second EEPROM 59 (program data set to be used to cope with an abnormality), is set again in the FPGA 56.

Further, there may also be adopted an FPGA configuration sequence in which when an abnormality occurs although the configuration is performed several times by using the program data of the first EEPROM 59, the selection determining portion 220 makes the configuration to be performed by using the second EEPROM 59 storing the program data set to be used to cope with the abnormality. This can be realized by such a way that an abnormality occurrence counter is prepared beforehand in the selection determining portion 220, and a switching SW 221 is switched when the abnormality occurs, for example, three times.

Next, as an example when an abnormality occurs in the F/B (feedback) system, there will be described an example to cope with the case where an error occurs in the encoder 30a, with reference to FIG. 12.

During the normal operation, the information from the encoder 30a is used as the data of the F/B system. Here, it is configured such that when an abnormality occurs in the encoder 30a, the data path through a switching SW 222 is switched, and the position control F/B is performed by using the data of the potentiometer 35. Since the reliability of data of the potentiometer 35 is usually inferior to that of the encoder 30a (due to the linearity, noise, and the like), the potentiometer 35 is used only at the time of calibration in which the potentiometer 35 is required for detecting an absolute position. However, it may also be configured such that the potentiometer 35 is used for an interim operation at the time when the abnormality occurs.

Next, there will be described a case where an error further occurs in the potentiometer 35 during the time when an abnormality is caused in the F/B system. When an abnormality occurs in the potentiometer 35, a balance with a calibration sequence is required. The potentiometer 35 is the only absolute position detecting unit. In the case where the clutch of the clutch mechanism portion 36 is disconnected, a difference between the endoscope bending position and the position of the remote control operation portion 7 may be caused. Therefore, when a clutch disconnecting instruction is issued to the clutch mechanism portion 36, in practice, the clutch is prevented from being disconnected, or a message to turn off the power supply is displayed on the monitor 6 at the time when the clutch is operated to be OFF. Further, since a maximum movable range restriction mechanical stopper (not shown) is provided on the side of the endoscope 2, it goes without saying that the operation may be performed under the relative position restriction even in the state where the position of the joystick of the remote control operation portion 7 is deviated from the bending position.

FIG. 13 shows a basic logical configuration block 250 relating to each block abnormality and state detection according to the present embodiment. Further, FIG. 14 shows a configuration (configuration which is used in the normal processing by the CPU or the like) in which the reset operation is performed by the WDT-CR when at least one abnormality is detected.

When some of the basic logical configuration blocks 250 are combined as shown in FIG. 16, by using the basic logical configuration block 250 as one unit, it is possible to configure a desired abnormal processing detecting portion 251 based on the combination of the logical product and the logical sum.

That is, the basic logical configuration block 250, which is configured by a NAND portion, a NOR portion, and a switching portion as shown in FIG. 13, is hence capable of configuring a basic logic of a Boolean algebra operation element. Various logical formulas can be formed by combining the basic logical configuration blocks 250.

The configuration of the present embodiment is difficult to be realized by the conventional CPU which performs a determined sequence. However, the present embodiment, the major component of which is the FPGA 56, can be hence easily realized by performing arrangement, wiring, and the like, of the basic logical configuration blocks as in the case of an electric circuit.

Further, the input is configured by the switching setting signal, an input 1, and an input 2, while the output is configured by one output. With this configuration, a more fundamental basic logical configuration block can be configured. For example, in the case of one input and one output, the input 1 may be connected as in the case of an electric circuit, and the switching setting signal may be fixed in order to use the basic logical configuration block as either the AND element or the OR element.

An application example of the abnormal processing detecting portion 251 configured by combining the basic logical configuration blocks 250 (1) to (n) is shown in FIG. 17. By configuring in the FPGA 56 the determining portion of monitoring signal of each block as will be described below, it is also possible to perform the switching operation to the normal position detecting unit at the time when an abnormality occurs in the F/B system (when an error occurs in the potentiometer 35 and the encoder 30a).

For example, the electric bending control operation is usually performed on the basis of the position control which controls the bending position in correspondence with the tilting angle of the joystick of the remote control operation portion 7. However, the electric bending control operation can also be performed by such a way that according to the occurrence of abnormality in the position control block 201a, the position control loop is bypassed and the servo control is performed by the speed control loop. In other words, it is possible to perform an operation to control the bending operation speed according to the tilting angle of the joystick.

Although not shown in detail, an action determined on the basis of each condition can be realized by operating wiring switching, and the like, arranged beforehand in the FPGA 56.

Up to the above description, the switching state at the time when an abnormality occurs is explained. In FIG. 15, there is shown an example of determination configuration in which the abnormality detection level is switched by combining the basic logical configuration blocks 250. In the above described configuration, the switching setting signal is fixed for each block abnormality and state detection. However, the error level can also be arbitrarily switched by connecting the switching setting signal of the first module (error level change determination logic module) to the output of another second module (abnormal state generation determination logic module).

The operation of the present embodiment configured in this way will be described. In the present embodiment, as shown in FIG. 18, when a power supply is turned on, the initial mode processing is first performed. Then, after the initial mode processing, the process proceeds to the mode switching processing.

In the mode switching processing, when the clutch is disconnected or when the bending operation start instruction is set to OFF at the time of completion of the initial mode processing, for example, the process proceeds to the calibration mode. Then, the process returns to the mode switching processing, when the clutch is again connected so that the instruction command value becomes coincident with the scope position, or when the bending operation start instruction is set to ON.

In the mode switching processing, when the operation mode is selected, the process proceeds to the operation mode, and the servo is set to ON. When the end of the operation mode is instructed, the process returns to the mode switching processing.

Here, the operation mode is a mode to perform an electric bending operation on the basis of an operation instruction from the remote control operation portion 7, and the maintenance mode is a mode to perform the setting (reading and writing) of parameters, the remote control based on the HMI mode in which a state monitor, or the like, is connected with a dedicated jig or a personal computer (described below), or the like.

Further, in the mode switching processing, when the maintenance mode is selected, the process proceeds to the maintenance mode, and the servo is set to ON. When the end of the maintenance mode is instructed, the process returns to the mode switching processing.

Further, in the mode switching processing, when a stop factor occurs, the process proceeds to the abnormal stop mode, and the servo is set to OFF.

The above described contents will be described in detail by using a flow chart shown in FIG. 19. When the power supply is turned on, the configuration of the FPGA 56 is performed by the EEPROM controller 102 in step S1. Subsequently, the initial mode processing (as will be described below) is performed in step S2, and the process waits for the completion of the initial mode processing in step S3.

When the initial mode processing is completed, a calibration request is generated by the operation mode controller 105 in step S4. Then, in step S5, it is determined whether or not the maintenance mode processing request is generated by the operation mode controller 105. When the maintenance mode processing request is generated, the maintenance mode processing (as will be described below) is performed in step S6, and the process returns to step S5.

When the maintenance mode processing request is not generated, it is determined in step S7 whether or not the operation mode controller 105 has returned to the mode switching processing from the maintenance mode processing. Then, when the operation mode controller 105 has returned to the mode switching processing, the calibration request is generated by the operation mode controller 105 in step S8, and the process returns to step S5.

When the operation mode controller 105 has not returned to the mode switching processing, the operation mode controller 105 determines in step S9 whether or not the calibration request is effective. When the calibration request is effective, the operation mode controller 105 performs the calibration processing, and determines in step S11 whether or not the calibration processing is normally completed. When the calibration processing is not normally completed, the operation mode controller 105 returns to step S5. When the calibration processing is normally completed, the operation mode controller 105 cancels the calibration request in step S12 and returns to step S5.

When determining that the calibration request is not effective in step S9, the operation mode controller 105 determines in step S13 whether or not the bending operation start instruction is set to OFF. When determining that the bending operation start instruction is set to OFF, the operation mode controller 105 generates the calibration request in step S14 and returns to step S5.

When determining that the bending operation start instruction is not set to OFF, the operation mode controller 105 determines in step S15 whether or not the clutch connection is OFF. When the clutch connection is OFF, the operation mode controller 105 proceeds to step S14. When the clutch connection is ON, the operation mode controller 105 performs the operation mode processing (as will be described below) in step S16 and returns to step S5.

Next, the initial mode processing will be described by using a flow chart shown in FIG. 20. The WDT 57 is first started in step S21. Then, the respective logical blocks initialize internal variables in step S22. The RL (right and left) motor current F/B portion 112, the UD (up and down) motor current F/B portion 113, the potentiometer control portion 114, and the thermistor control portion 115 start the data sampling in step S23, respectively.

Then, in step 24, the communication is started by the serial communication unit 100 and the serial communication control portion 101. In step 25, it is determined whether or not the external hardware is normal. When the external hardware is abnormal, the abnormal stop mode processing is performed in step S26.

When it is determined that the external hardware is normal, the motor controller 110 determines in step S27 whether or not the offset of motor current is normal. When the offset of motor current is abnormal, the motor controller 110 performs the abnormal stop mode processing in step S26.

When determining that the offset of motor current is normal, the motor controller 110 detects the rotor position of the motor 30 in step S28, and reads parameters in the DPRAM 106 in step S29.

Next, the motor controller 110 determines in step S30 whether or not all the read parameter values are "0". When all the parameter values are not "0", the motor controller 110 ends the processing as it is. When all the parameter values are "0", the motor controller 110 writes the default value of the parameter in the DPRAM 106 in step S31 and ends the processing.

Next, the maintenance mode processing will be described by using a flow chart shown in FIG. 21. The operation mode controller 105 starts to update with the jig (not shown). The operation mode controller 105 determines in step S41 whether or not the servo-ON request is generated by the jig. When there is the servo-ON request in step S42, the operation mode controller 105 sets the servo to ON and returns to step S41.

Similarly, the operation mode controller 105 determines in step S43 whether or not the servo OFF request is generated by the jig. When there is the servo OFF request in step S44, the operation mode controller 105 sets the servo to OFF and returns to step S41.

Next, the operation mode controller 105 determines in step S45 whether or not the HMI mode (monitor mode for monitoring the servo state) request is generated by the jig. When there is the HMI mode request in step S46, the operation mode controller 105 performs the HMI mode processing and returns to step S41.

Then, the operation mode controller 105 determines in step S47 whether or not the first maintenance request is generated by the jig. When there is the first maintenance request in step S48, the operation mode controller 105 performs the sinusoidal wave output mode processing and returns to step S41.

Subsequently, the operation mode controller 105 determines in step S49 whether or not the second maintenance request is generated by the jig. When there is the second maintenance request in step S50, the operation mode controller 105 performs the torque control mode processing and returns to step S41.

Further, the operation mode controller 105 determines in step S51 whether or not the third maintenance request is generated by the jig. When there is the third maintenance request in step S52, the operation mode controller 105 performs the speed control mode processing and returns to step S41.

Further, the operation mode controller 105 determines in step S53 whether or not the fourth maintenance request is generated by the jig. When there is the fourth maintenance request in step S54, the operation mode controller 105 performs the position control mode processing and returns to step S41.

Next, the operation mode controller 105 determines in step S55 whether or not the fifth maintenance request is generated by the jig. When there is the fifth maintenance request in step S56, the operation mode controller 105 performs the analog input position control mode and returns to step S41.

Further, the operation mode controller 105 determines in step S57 whether or not the sixth maintenance request is generated by the jig. When there is the sixth maintenance request in step S58, the operation mode controller 105 performs the scope limit adjustment mode processing and returns to step S41.

Subsequently, the operation mode controller 105 determines in step S59 whether or not the seventh maintenance request is generated by the jig. When there is the seventh maintenance request in step S60, the operation mode controller 105 performs the lap operation mode processing and returns to step S41.

Here, the lap operation mode is a mode to make a predetermined bending operation performed, for example, a mode to make a sequential operation RL→UD→RL, and the like, performed.

Next, the operation mode controller 105 determines in step S61 whether or not the eighth maintenance request is generated by the jig. When there is the eighth maintenance request in step S62, the operation mode controller 105 performs the calibration adjustment mode processing and returns to step S41.

As described above, it is possible to independently confirm the operation of each function required for the electric bending operation.

Next, the calibration mode processing will be described by using a flow chart shown in FIG. 22. The operation mode controller 105 determines in step S81 whether or not the clutch connection is OFF. When the clutch connection is OFF, the operation mode controller 105 sets the servo to OFF, and proceeds to step S83. When the clutch connection is not OFF, the operation mode controller 105 proceeds to step S83 as it is.

Then, the operation mode controller 105 determines in step S83 whether or not the clutch connection is ON. When the clutch connection is ON, the operation mode controller 105 proceeds to step S84. When the clutch connection is not ON, the operation mode controller 105 returns to step S81.

Then, the operation mode controller 105 determines in step S84 whether or not the operation amount and the present position are in a predetermined range. When the operation amount and the present position are in the predetermined range, the operation mode controller 105 proceeds to step S85. When the operation amount and the present position are not in the predetermined range, the operation mode controller 105 returns to step S81.

Then, the operation mode controller 105 determines in step S85 whether or not the bending operation start instruction is set to ON. When the bending operation start instruction is set to ON, the operation mode controller 105 ends the processing. When the bending operation start instruction is not set to ON, the operation mode controller 105 returns to step S81.

Next, the operation mode processing will be described by using a flow chart shown in FIG. 23 and with reference to a timing chart shown in FIG. 24. First, in step S71, the servo is set to ON. In step S72, it is determined whether or not the process is in the torque control cycle event period. When the process is in the torque control cycle event period, the torque control calculation processing is performed in step S73, and the process returns to step S72. When the process is not in the torque control cycle event period, the process proceeds to step S74.

In step S74, it is determined whether or not the process is in the position and speed control event period. When the process is in the position and speed control event period, the position and speed control calculation processing is performed in step S75, and the process returns to step S72. When the process is not in the position and speed control event period, the process proceeds to step S76. Then, in step S76, it is determined whether or not the servo abnormality is detected. When the servo abnormality is detected, the abnormal stop mode processing is performed in step S77. When the servo abnormality is not detected, the process returns to step S72.

As described above, in the present embodiment, the electric bending control is performed by separating the processing into logical blocks by means of the FPGA. Thus, in the present embodiment, unlike the conventional sequential control using a microprocessor, even when an abnormality occurs in a part of the servo systems, all the control system is not stopped, and a servo system can be effectively selected. Therefore, it is possible to improve the operability without the examination being interrupted.

Note that in the present embodiment, the control portion 37 is provided in the bending control portion 10b of the endoscope 2, but the present invention is not limited to this. The control portion 37 may be provided in the image processing apparatus 4, or may be provided in a separate controller apparatus.

The present invention is not limited to the above described embodiment, and various modification, changes or the like, are possible within the scope and spirit of the invention.

What is claimed is:

1. An electric bending endo scope comprising:
    a bending portion provided in an insertion portion;
    a bending drive unit having a plurality of components for effecting a bending operation of the bending portion;
    a bending power unit configured to drive the bending drive unit;
    a bending state detecting unit configured to detect operation information of the bending drive unit, and to detect bending state information of the bending portion;
    an instruction unit configured to output bending instruction information for bending the bending portion;
    a bending operation control unit configured by a plurality of independent logical blocks to output a control signal for controlling a bending state of the bending portion to the bending power unit based on the bending instruction information of the instruction unit;
    a block monitoring unit configured to monitor a control state of the plurality of independent logical blocks configuring the bending operation control unit; and
    a logical block selecting unit configured, based on a monitoring result of the block monitoring unit, when at least one of a speed control block, a torque control block, and a position control block among the plurality of independent logical blocks becomes inoperable, to switch a switch portion provided in a circuit which electrically connects the speed control block, the torque control block, and the position control block, and set a gain setting value, to thereby make a closed loop characteristic remain the same,
    wherein, when it is determined that a control state of the speed control block is abnormal by the block monitoring unit, the switch portion removes only the speed control block from the circuit, and sets the gain setting value by the position control block, to thereby make the closed loop characteristic remain the same.

2. The electric bending endoscope according to claim 1, wherein at least one of the plurality of independent logical blocks includes:
    a bending state information input logical block configured to acquire the bending state information detected by the bending state detecting unit; and
    a state calculation logical block configured to perform a calculation based on the bending state information acquired by the bending state information input logical block and the bending instruction information.

3. The electric bending endoscope according to claim 1, wherein the block monitoring unit and the logical block selecting unit are configured by the plurality of independent logical blocks.

4. The electric bending endoscope according to claim 2,
    wherein the bending state information includes bending position information on the bending portion, and
    wherein the state calculation logical block further at least includes:
        a position information calculation logical block configured to calculate a difference between the bending position information and the bending instruction information, and to calculate position deviation information;
        a speed information calculation logical block configured to calculate a temporal change rate of the bending position information; and
        a position information calculation logical block configured to calculate position information on the bending portion.

5. The electric bending endoscope according to claim 1, wherein each of the plurality of independent logical blocks has a function whose logic can be reconfigured.

6. The electric bending endoscope according to claim 2, wherein each of the plurality of independent logical blocks has a function whose logic can be reconfigured.

7. The electric bending endoscope according to claim 5, wherein the bending operation control unit is configured by an FPGA.

8. An electric bending endoscope comprising:
    a bending portion provided in an insertion portion;
    a bending drive unit having a plurality of components for effecting a bending operation of the bending portion;
    a bending power unit configured to drive the bending drive unit;
    a bending state detecting unit configured to detect operation information of the bending drive unit, and to detect bending state information of the bending portion;
    an instruction unit configured to output bending instruction information for bending the bending portion;
    a bending operation control unit configured by a plurality of independent logical blocks to output a control signal for controlling a bending state of the bending portion to the bending power unit based on the bending instruction information of the instruction unit;
    a block monitoring unit configured to monitor a control state of the plurality of independent logical blocks configuring the bending operation control unit; and
    a logical block selecting unit configured, based on a monitoring result of the block monitoring unit, when at least one of a speed control block, a torque control block, and a position control block among the plurality of independent logical blocks becomes inoperable, to switch a switch portion provided in a circuit which electrically connects the speed control block, the torque control block, and the position control block, and set a gain setting value, to thereby make a closed loop characteristic remain the same,
    wherein each of the speed control block, the position control block, and the torque control block includes a plurality of control blocks as same components, and when it is determined that an abnormality occurs in at least one of the plurality of independent logical blocks by the block monitoring unit, the switch portion switches data flow among the speed control block, the position control block, and the torque control block.

* * * * *

UNITED STATES PATENT AND TRADEMARK OFFICE
CERTIFICATE OF CORRECTION

| | | |
|---|---|---|
| PATENT NO. | : 8,622,895 B2 | Page 1 of 1 |
| APPLICATION NO. | : 12/167628 | |
| DATED | : January 7, 2014 | |
| INVENTOR(S) | : Toshimasa Kawai | |

It is certified that error appears in the above-identified patent and that said Letters Patent is hereby corrected as shown below:

In the Claims

It should read:

Column 15, line 5 (claim 1): An electric bending endoscope comprising:

Signed and Sealed this
Third Day of June, 2014

Michelle K. Lee
*Deputy Director of the United States Patent and Trademark Office*